(12) United States Patent
Howard et al.

(10) Patent No.: US 7,120,939 B1
(45) Date of Patent: Oct. 17, 2006

(54) SUPPORT FOR A FACE SHIELD

(75) Inventors: Jeremy Conrad Howard, Little Compton, RI (US); Richard W. Canavan, Woodstock, CT (US); Luke William Michas, Niceville, FL (US); Raymond Curci, Smithfield, RI (US); Laurent Froissard, Cranston, RI (US)

(73) Assignee: Bacou-Dalloz Eye & Face Protection, Inc., Smithfield, RI (US)

( * ) Notice: Subject to any disclaimer, the term of this patent is extended or adjusted under 35 U.S.C. 154(b) by 0 days.

(21) Appl. No.: 10/868,525

(22) Filed: Jun. 15, 2004

Related U.S. Application Data

(63) Continuation-in-part of application No. 10/700,940, filed on Nov. 4, 2003, now Pat. No. 7,007,306.

(51) Int. Cl.
*A42B 3/00* (2006.01)

(52) U.S. Cl. .................. 2/416; 2/417; 2/418

(58) Field of Classification Search .............. 2/416, 2/420, 452, 453, DIG. 11, 8, 9, 417, 418, 2/419, 424, 10, 8.1; 128/201.22, 201.23, 128/201.24, 207.17
See application file for complete search history.

(56) References Cited

U.S. PATENT DOCUMENTS

| | | | | | |
|---|---|---|---|---|---|
| 631,880 | A | * | 8/1899 | Ross | 2/418 |
| 1,601,830 | A | * | 10/1926 | Huntsman | 2/8 |
| 2,194,492 | A | * | 3/1940 | Bowers | 2/8 |
| 2,272,833 | A | * | 2/1942 | Dockson | 2/8 |
| 2,283,120 | A | | 5/1942 | Malcom | |
| 2,320,244 | A | * | 5/1943 | Maillart | 2/8 |
| 2,326,376 | A | * | 8/1943 | Markgraf, Jr. et al. | 2/8 |
| 2,360,482 | A | * | 10/1944 | Evans | 2/8 |
| 2,390,006 | A | * | 11/1945 | Severy | 2/8 |
| 2,396,239 | A | * | 3/1946 | Beck | 2/8 |
| 2,397,722 | A | * | 4/1946 | Bowers | 2/8 |
| 2,445,203 | A | * | 7/1948 | Bowers | 2/10 |
| 2,526,582 | A | * | 10/1950 | James | 2/8 |
| 2,594,335 | A | * | 4/1952 | Moeller | 16/334 |
| 2,658,200 | A | * | 11/1953 | Bowers, Sr. | 2/8 |
| 2,758,307 | A | * | 8/1956 | Treiber | 2/9 |
| 2,763,006 | A | * | 9/1956 | Amundsen | 2/8 |
| 3,026,525 | A | * | 3/1962 | Gyorfy | 2/8 |
| 3,047,876 | A | * | 8/1962 | Malcom, Jr. | 2/9 |
| 3,075,201 | A | * | 1/1963 | Lindblom | 2/8 |
| 3,181,532 | A | * | 5/1965 | Artell | 128/201.23 |
| 3,259,908 | A | | 7/1966 | Simpson et al. | |
| 3,430,262 | A | * | 3/1969 | Raschke | 2/8 |
| 3,430,263 | A | * | 3/1969 | Newcomb | 2/8 |

(Continued)

Primary Examiner—Rodney Lindsey
(74) Attorney, Agent, or Firm—Salter & Michaelson

(57) ABSTRACT

A face shield support includes an adjustable frame which fits over the head of a user during use and provides support for the face shield frame. In one embodiment, the frame includes a first, or frontal strap that extends from approximately above the ears of the user and across the forehead of the user, and a second or rear adjustable strap extending from approximately above the ears of the user and around the base of the user's head adjacent the occipital lobe. Connecting the rear and frontal straps are a pair of mounting members which secure the face shield frame to the support and which also pivotally connect the frontal and rear adjustable straps. An upper bridge may also be provided which extends over the top portion of a user's head and further secures the frontal and rear straps together. The frontal strap may optionally included an expanded frontal area for additional comfort.

11 Claims, 28 Drawing Sheets

U.S. PATENT DOCUMENTS

| | | | |
|---|---|---|---|
| 3,555,560 A * | 1/1971 | Rascke ........................ 2/416 |
| 3,696,442 A * | 10/1972 | Amundsen et al. ................ 2/8 |
| 3,789,428 A | 2/1974 | Martin |
| 4,056,852 A * | 11/1977 | Greendale .................... 2/417 |
| 4,076,373 A | 2/1978 | Moretti |
| 4,097,929 A | 7/1978 | Lowe et al. |
| 4,101,980 A | 7/1978 | Stepan et al. |
| 4,462,119 A | 7/1984 | Rudd |
| 4,464,800 A * | 8/1984 | Edwards ...................... 2/452 |
| 4,507,809 A | 4/1985 | Stepan |
| 4,536,892 A * | 8/1985 | Brinkhoff et al. ............. 2/424 |
| 4,542,538 A | 9/1985 | Moretti et al. |
| 4,748,695 A | 6/1988 | Shigematsu et al. |
| 4,888,831 A | 12/1989 | Oleson |
| D320,870 S | 10/1991 | Asbury et al. |
| 5,077,836 A | 1/1992 | Idoff et al. |
| 5,410,757 A | 5/1995 | Vienamo et al. |
| 5,412,811 A * | 5/1995 | Hildenbrand et al. ........... 2/10 |
| 5,571,217 A * | 11/1996 | Del Bon et al. .................. 2/9 |
| 5,793,449 A | 8/1998 | Lagerwall |
| D416,649 S | 11/1999 | Burns et al. |
| 6,102,033 A | 8/2000 | Baribeau et al. |
| 6,154,881 A | 12/2000 | Lee |
| 6,317,895 B1 | 11/2001 | Erth et al. |
| 2005/0091732 A1* | 5/2005 | Howard et al. ............... 2/424 |

\* cited by examiner

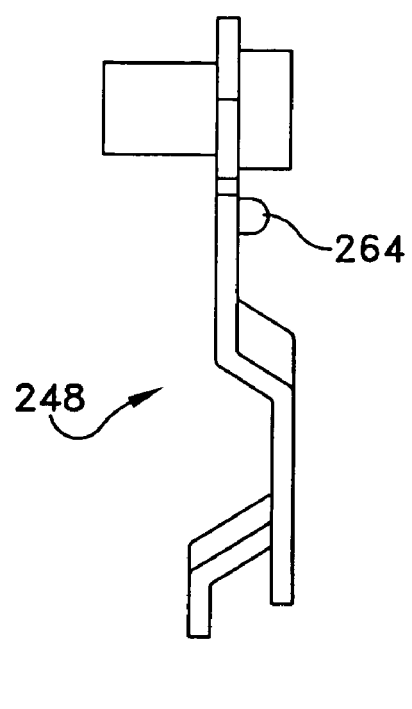
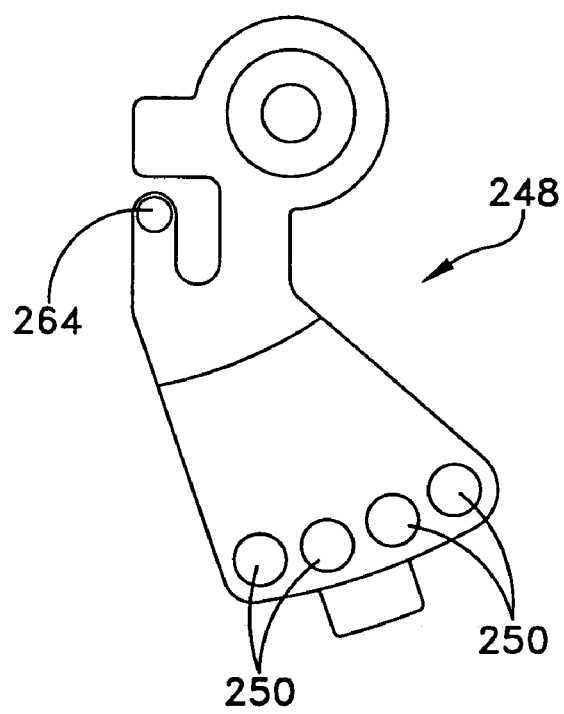
FIG. 26
FIG. 27

SUPPORT FOR A FACE SHIELD

1. CROSS REFERENCE TO RELATED APPLICATIONS

This application is a continuation-in-part of U.S. Ser. No. 10/700,940 filed on Nov. 4, 2003 now U.S. Pat. No. 7,007,306.

2. TECHNICAL FIELD

The present disclosure is directed to a face shield support, and, more particularly to an improved face shield support for supporting a face shield which is readily adjustable by a user.

3. BACKGROUND

The use of face shields to protect a user's eyes and face from various occupational hazards is well known in the art. Face shields are used in numerous professions as protective equipment including, for example, in the chemical, medical, construction, and manufacturing fields. Face shields are typically supported on a user's head by a headband, visor, or helmet, or other type of support system, with the face shield attached such that it is positioned in front of the user's face during operation. Many known supports allow the face shield to pivot from a lowered position (during use) to an upward position (when not in use) so that the face shield does not have to be entirely removed when not in use. It is also common for face shields to be worn for extended periods of time. As such, it is desirable that the face shield support be comfortable to wear. In addition, the face shield should be positioned to provide adequate protection while not obstructing visibility. In order to provide for the proper fit, the support should be adjustable in order to accommodate variations in the size and shape of different user's heads. As will be appreciated, proper fit of the face shield over the user's head is desirable because it aids in both the comfort and proper positioning of the face shield.

While a variety of face shield supports exist today, there is a continued need in the art for additional face shield supports that have lasting comfort, which provide the desired positioning of the face shield for a variety of users, and which are simple to use.

SUMMARY

The face shield supports disclosed herein provide an adjustable support to position a face shield on a variety of users. The support can hold the face shield in an up, or out of use position, and a down, or in use position. The face shield support includes an adjustable frame which fits over the head of a user during use and which provides support for the face shield. In one embodiment, the adjustable frame includes a first, or frontal strap that extends from approximately above the ears of the user and across the forehead of the user, and a second or rear adjustable strap extending from approximately above the ears of the user and around the base of the user's head adjacent the occipital lobe. Connecting the rear and frontal straps are a pair of mounting members which secure the face shield to the support and which also pivotally connect the frontal and rear adjustable straps. An upper bridge may also be provided which extends over the top portion of a user's head and further secures the frontal and rear straps together. The frontal strap may optionally include an expanded frontal area for additional comfort. Padding may also be provided on an inner surface of both the frontal and rear straps, adjacent the forehead and base of the user's head. In use, the face shield support distributes the pressure form the face shield frame around the head of the user. Both the rear and frontal straps are pivotally connected so that the frontal strap may be raised and lowered in order to raise and lower the face shield frame. The rear strap preferably includes a first end and a second end which can be adjusted in order to change the overall circumference of the face shield support. By providing pivoting of the frontal strap, the face shield may be readily raised and lowered, as desired while the provision of an adjustable rear strap accommodates varying head widths. In another embodiment, the face shield support allows the distance between the lens of the face shield and the user's face to be readily varied by the user.

BRIEF DESCRIPTION OF THE DRAWINGS

It should be understood that the drawings are provided for the purpose of illustration only and are not intended to define the limits of the invention. The foregoing and other objects and advantages of the embodiments described herein will become apparent with reference to the following detailed description when taken in conjunction with the accompanying drawings in which:

FIG. 26 is a side view of a mounting element of FIG. 22;

FIG. 27 is a front view of the mounting element of FIG. 26;

DETAILED DESCRIPTION OF THE ILLUSTRATIVE EMBODIMENTS

Figure 1:
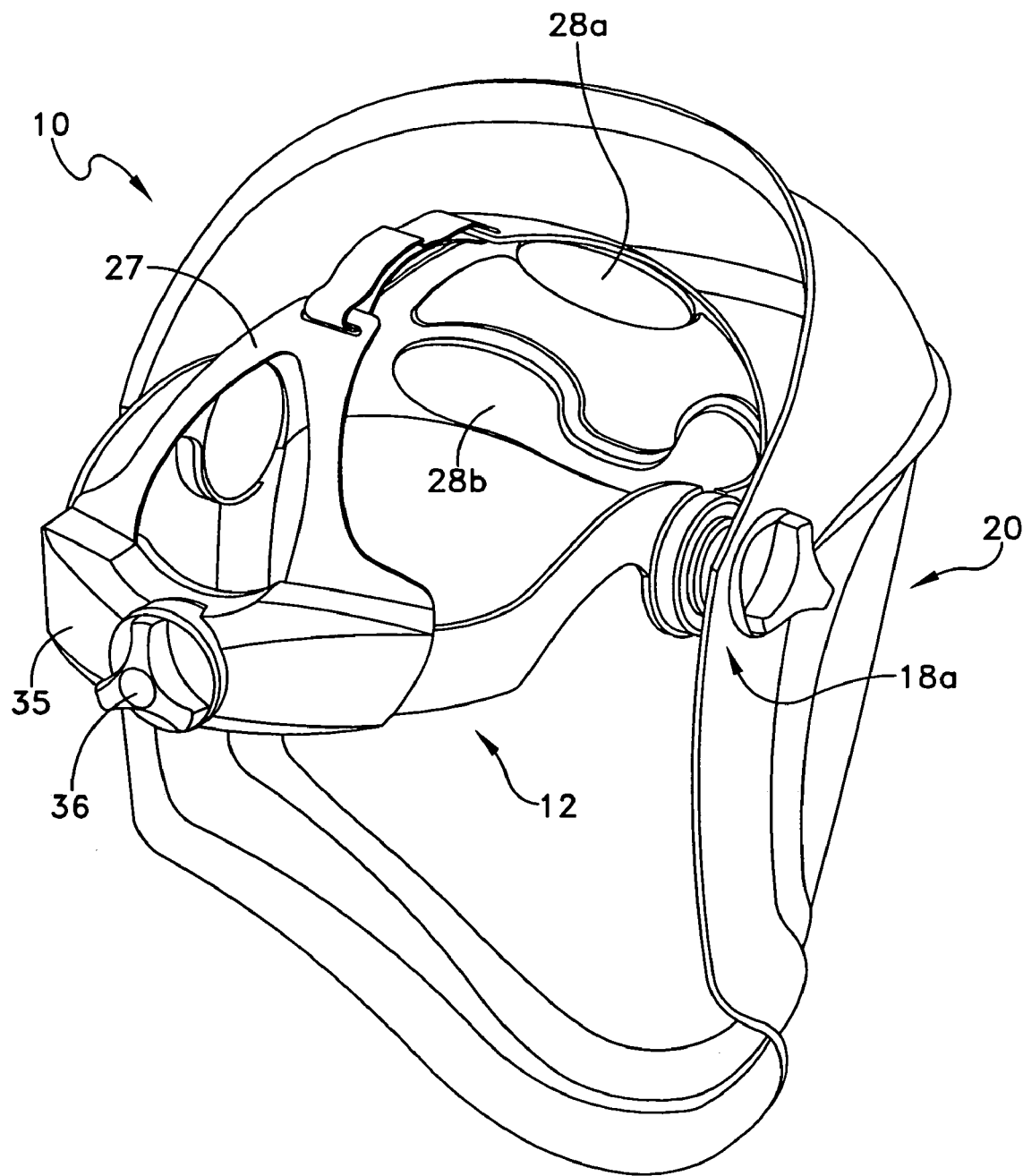
FIG. 1 is a rear perspective view of a first embodiment of a face shield supporting a face shield.

A first embodiment of a face shield support 10 for supporting a face shield is illustrated in FIGS. 1–14. The face shield support 10 includes an adjustable frame 12 sized to fit over the head of a user and which provides support for the face shield. In the present embodiment, the frame 12 includes a first, or frontal strap 14 that preferably extends from approximately above the ears of the user and across the forehead of the user, and a second or rear adjustable strap 16 that preferably extends from approximately above the ears of the user and around the base of the user's head over the occipital lobe. Connecting the rear and frontal straps are a pair of mounting members 18a, 18b which secure the face shield 20 to the support 10 and which also pivotally connect the frontal and rear adjustable straps 14, 16.

Figure 2:
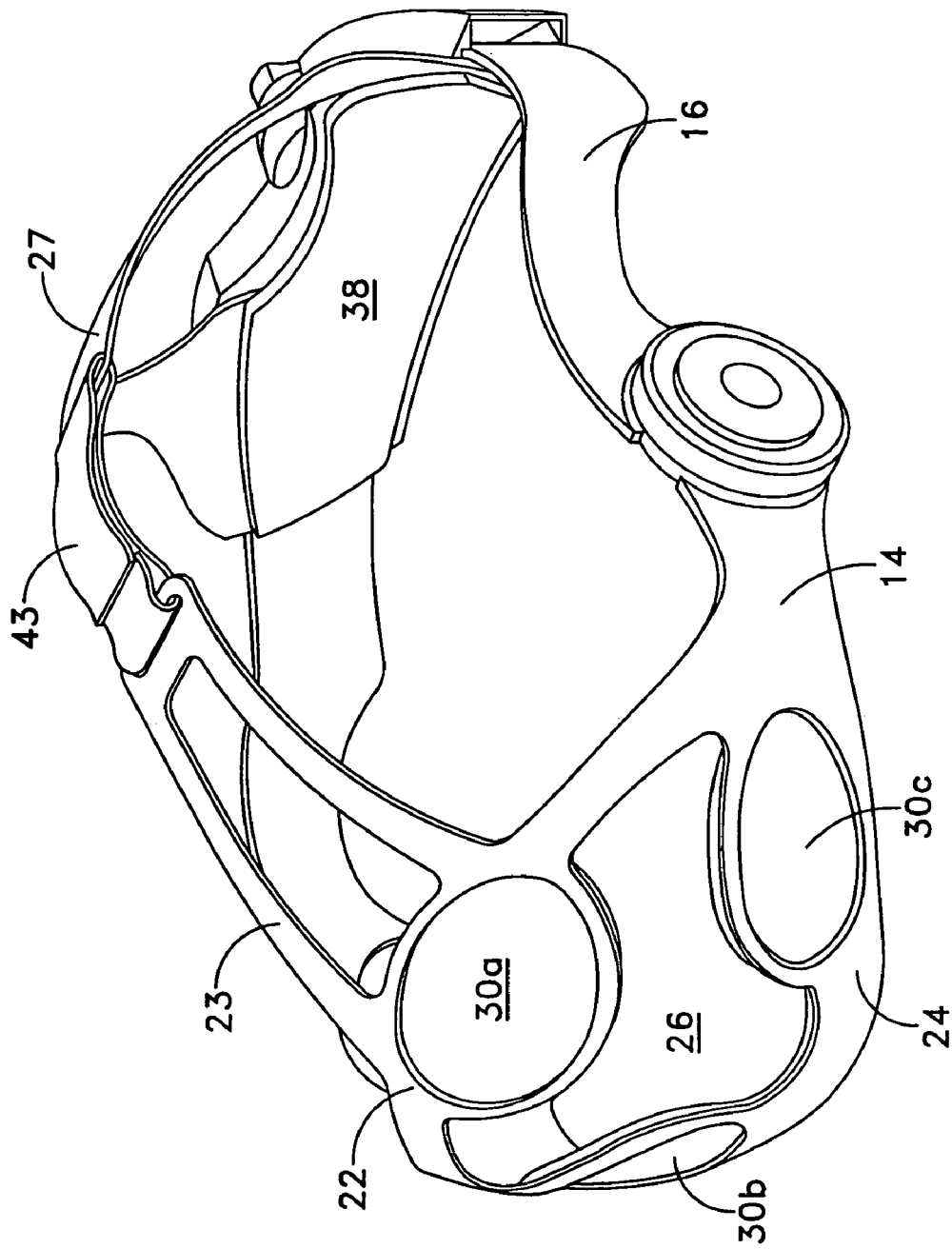
FIG. 2 is a front perspective view of the face shield support of FIG. 1.
Figure 4:
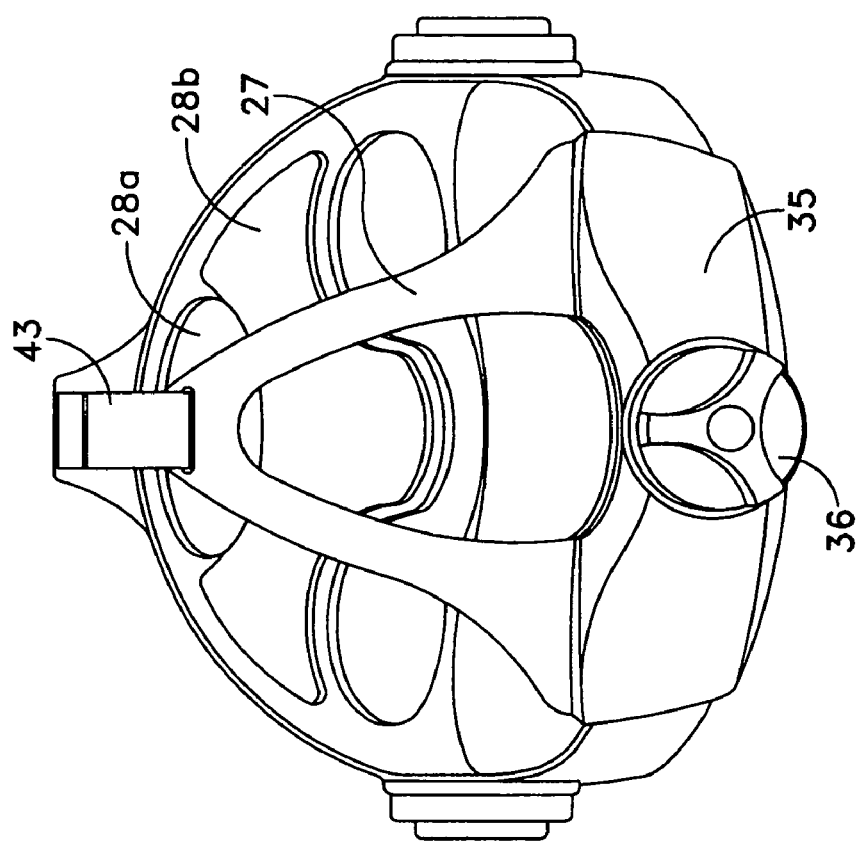
FIG. 4 is a rear elevational of the face shield support of FIG. 1.
Figure 3:
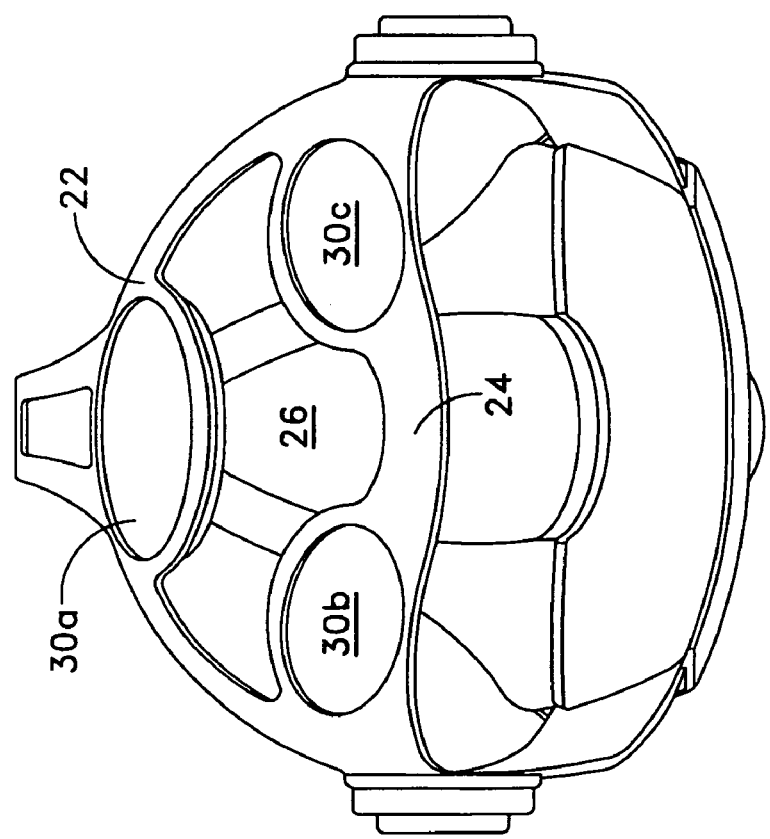
FIG. 3 is a front elevational of the face shield support of FIG. 1.
Figure 5:
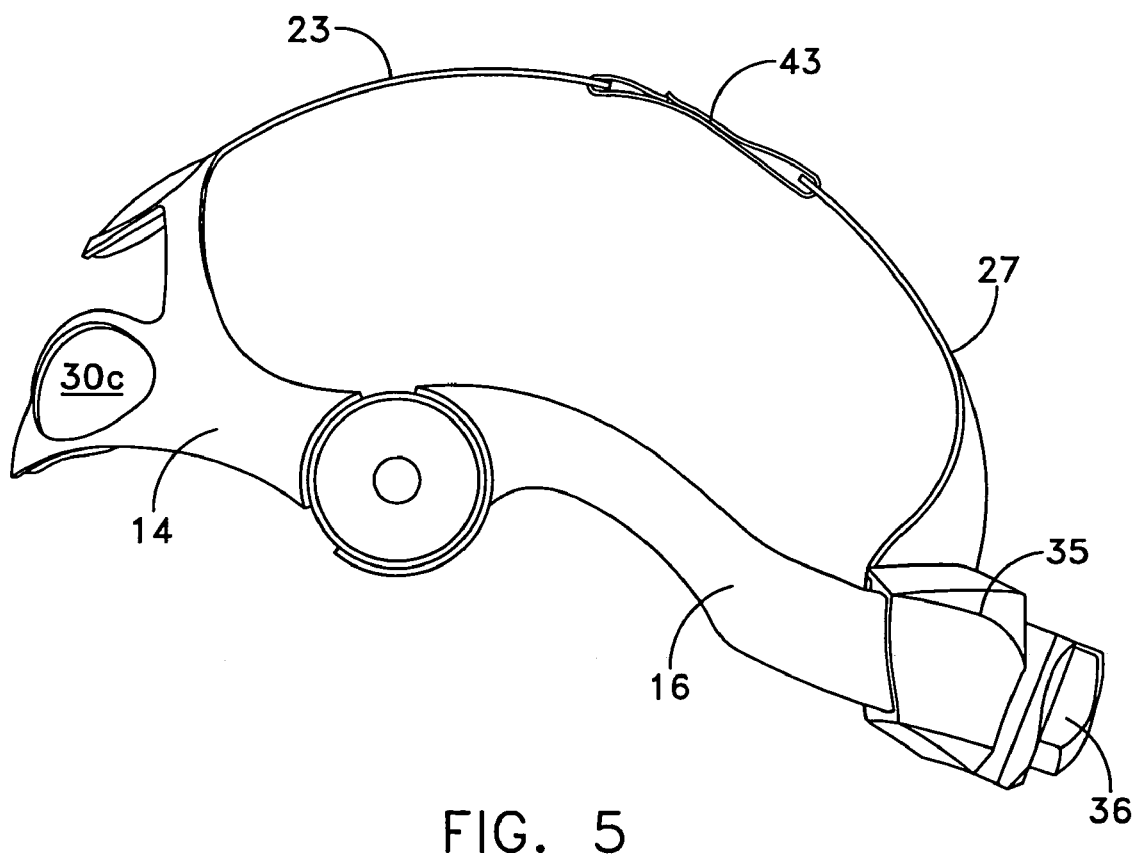
FIG. 5 is a side elevational of the face shield support of FIG. 1.
Figure 7:
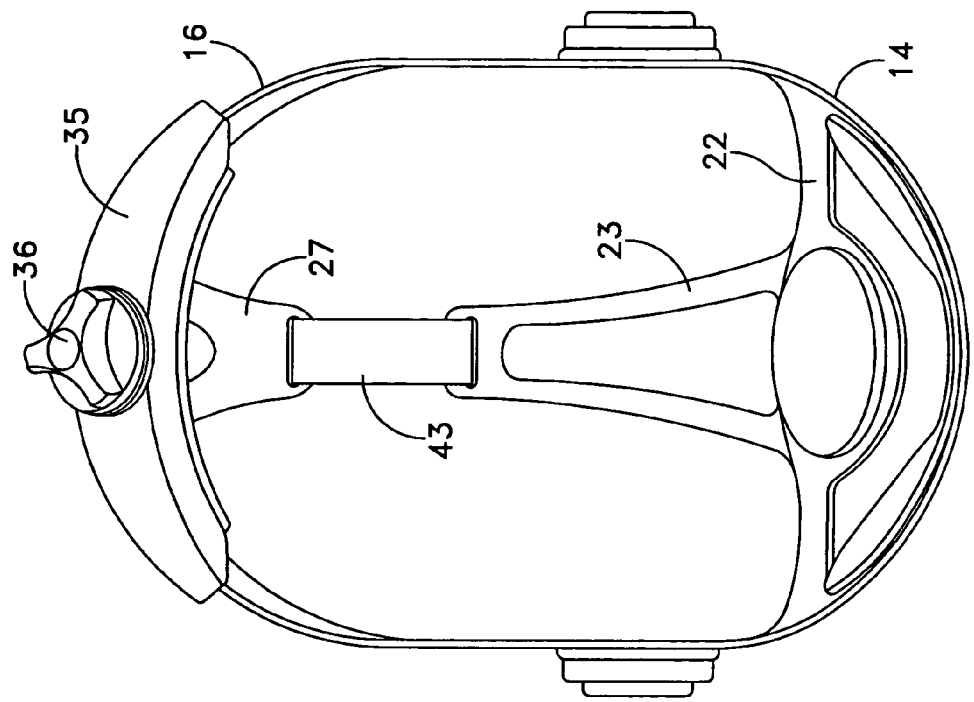
FIG. 7 is a bottom plan view of the face shield support of FIG. 1.
Figure 6:
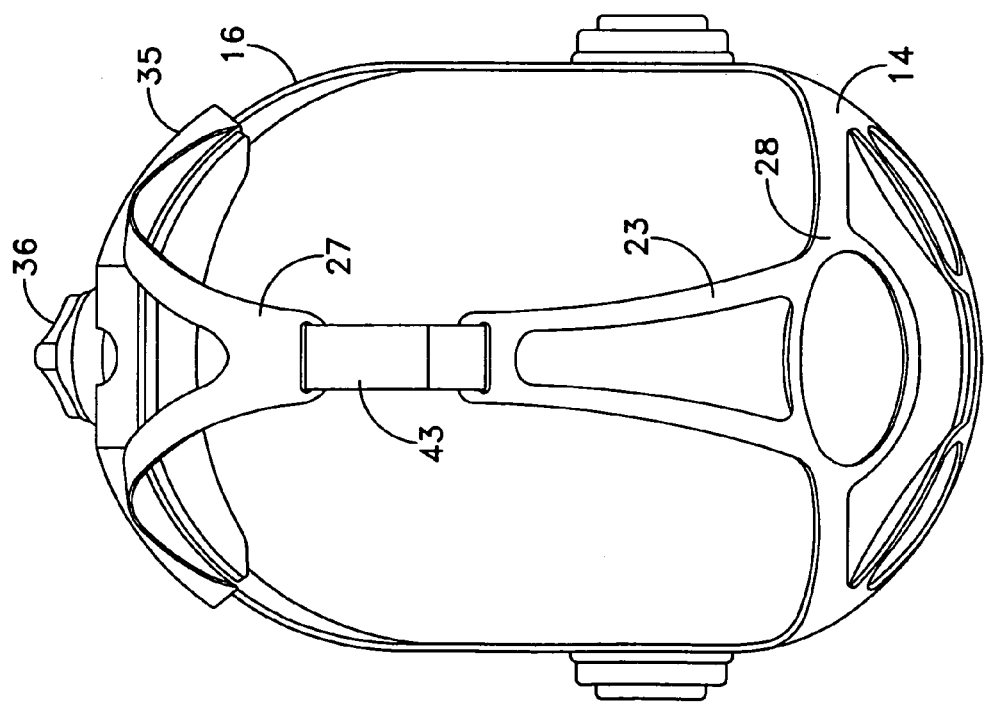
FIG. 6 is a top plan view of the face shield support of FIG. 1.
Figure 8:
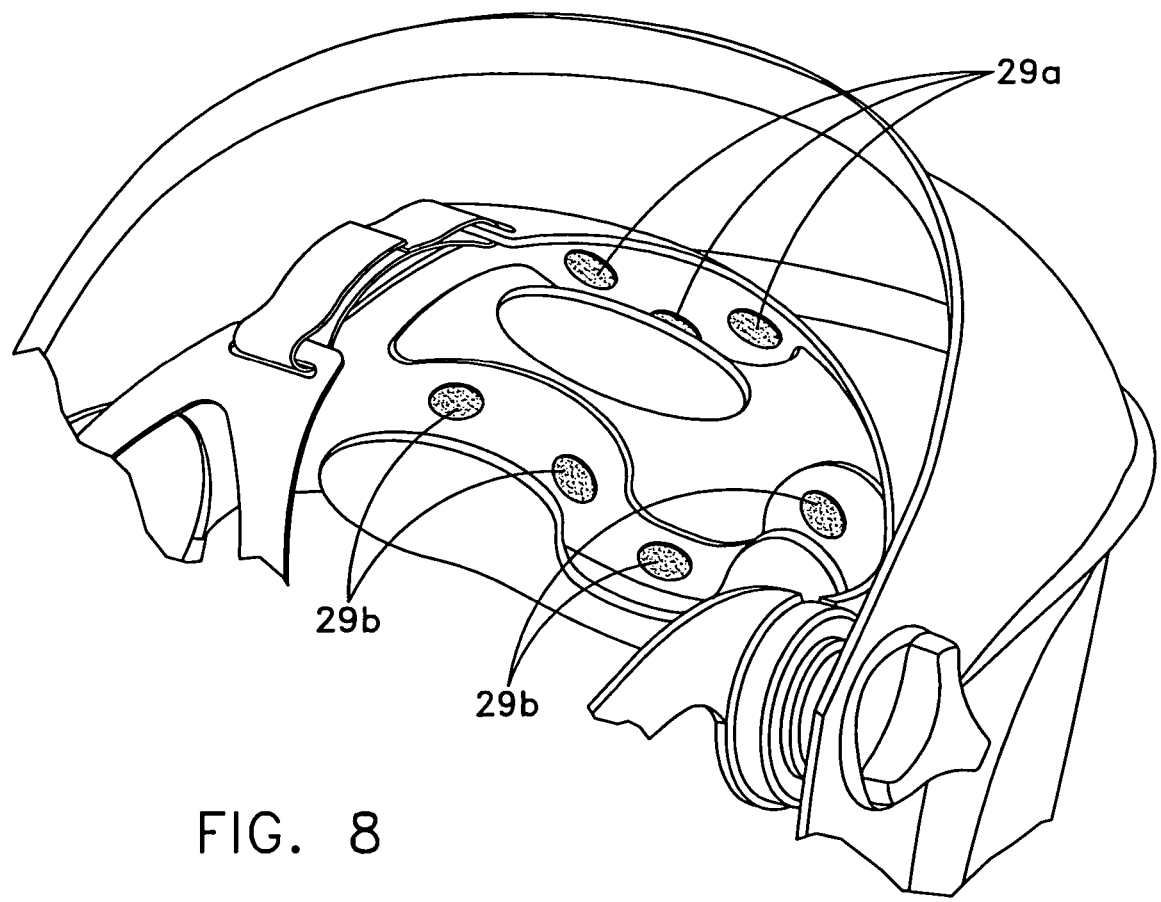
FIG. 8 is an enlarged view of the inside of the front of the face shield support of FIG. 1.

As best shown in FIGS. 2–3, the frontal strap 14 may include an upper portion 22 and a lower portion 24 which together form a generally triangular configuration. This expanded frontal area may be provided in order to distribute the pressure on the front of the wearer's head. In the present embodiment, an opening 26 is disposed between the upper portion 22 and the lower portion 24 which allows air to circulate. Alternatively, the upper and lower portions of the expanded frontal area may be formed as a solid, unitary member (not shown). By having an upper and lower portion, the support member sits more securely on the head of the user, as described in more detail below. In addition, the weight of the face shield is more evenly distributed which prevents concentration of pressure from the face shield on a single point on the forehead of the wearer. The upper portion 22 may also support a frontal bridge portion 23 for attachment with a rear bridge portion 27. The frontal and rear bridge portions help secure the support over the head of the wearer, as also described in greater detail below. Pads 28a, 28b may be positioned on an inside surface of both the upper and lower portions of the frontal strap as shown in FIGS. 1 and 4, or a plurality of smaller pads 29a and 29b may be utilized as shown in FIG. 8. The pads provide additional cushioning between the support and the wearer and may aid with absorption of sweat. The outer surface of the frontal strap may include recessed areas 30a, 30b, 30c for receiving stickers, indicia or the like.

Frontal strap 14 may be pivotally attached to rear strap 16 by mounting members 18a, 18b. In the present embodiment, the mounting members each include an outer collar 17 which is rotatably connected to an inner collar 19. See FIG. 12. The frontal strap 14 is preferably supported on the outer collar 17 and is rotatable relative to the inner collar when the side knobs 21 are loose. A fastener 40, which may be a screw, is provided through the collars and is received within each of the side knobs. As the side knobs 21 are turned on the fasteners, movement between the frontal strap and the rear strap is restricted. Once the knobs are sufficiently tightened, the frontal strap is held in position. The mounting members 18a, 18b are also used to support the face shield 20 on the support member 10. In particular, the fasteners 40 are received within opening 42 disposed on either side of the face shield 20 and is then received within the side knobs 21 which are supported on the outer surface of the face shield. In this manner, the face shield 20 is sandwiched between the side knobs 21 and the outer collar 17 as the knobs 21 are tightened.

Figure 9:
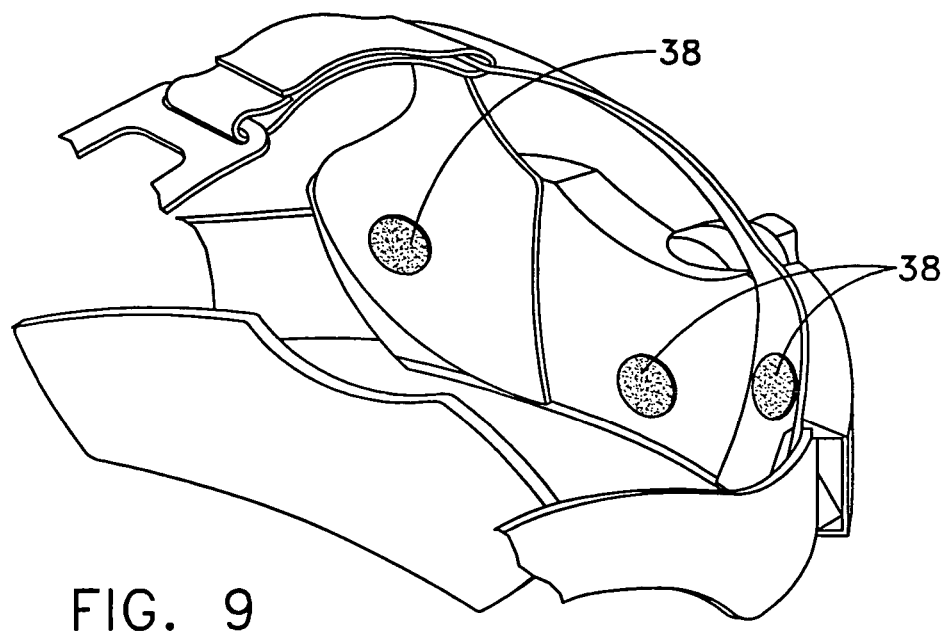
FIG. 9 is an enlarged view of the inside of the rear of the face shield support of FIG. 1.
Figure 13:
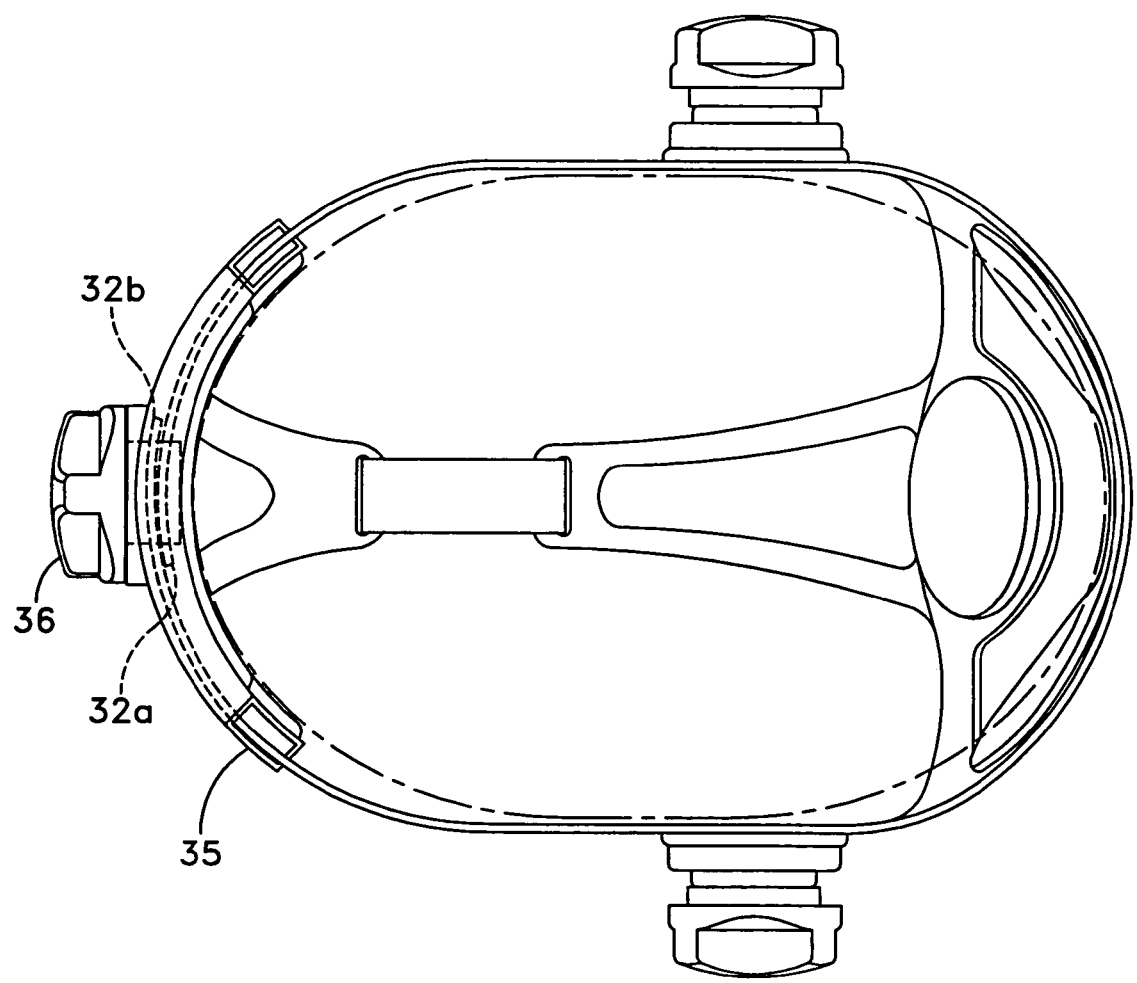
FIG. 13 is a top view of the face shield support of FIG. 10.
Figure 14:
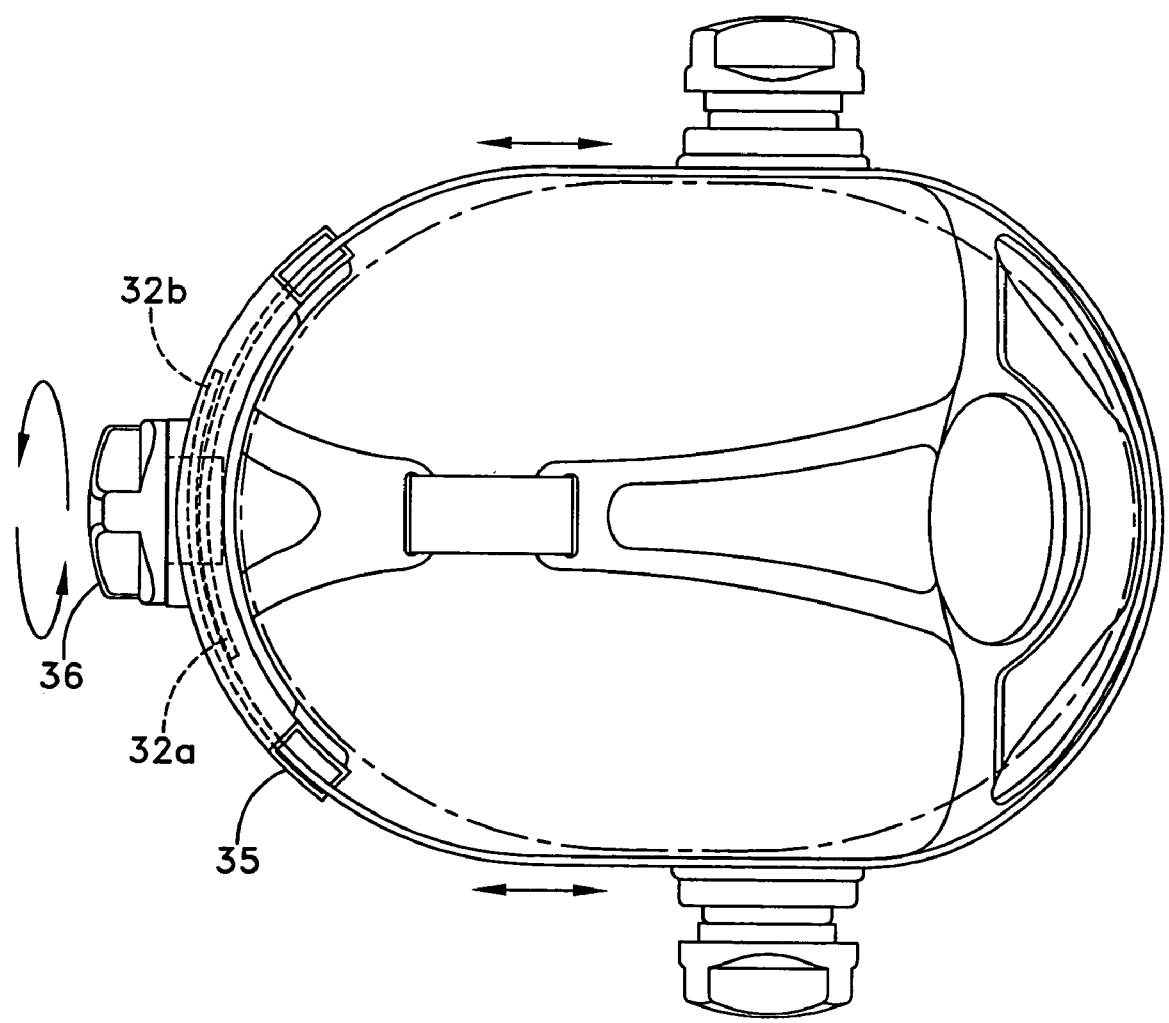
FIG. 14 is a top view of the face shield support of FIG. 10 showing variations in the circumference of the support.
Figure 15:
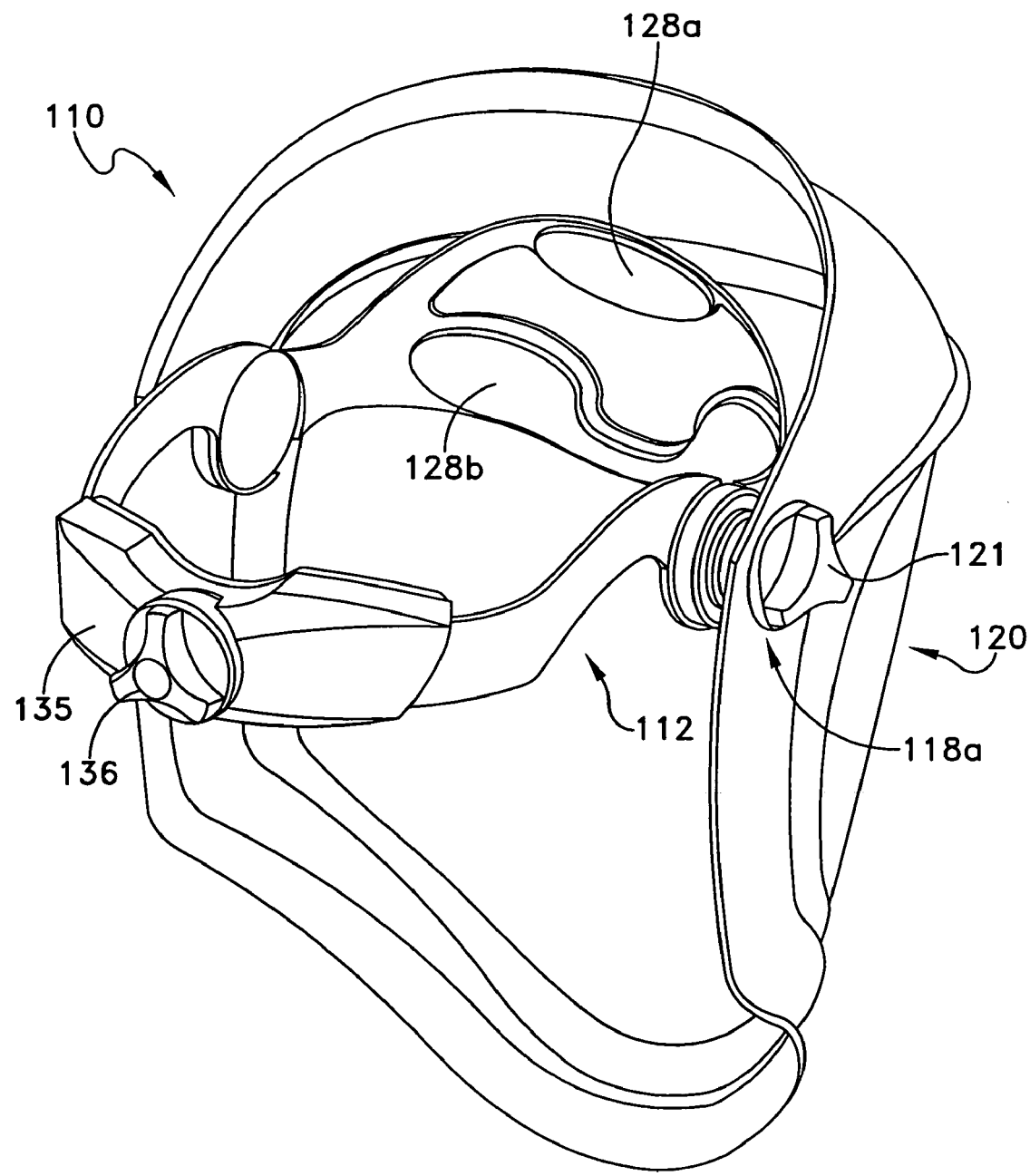
FIG. 15 is a rear perspective view of a second embodiment of a face shield support supporting a face shield.
Figure 16:
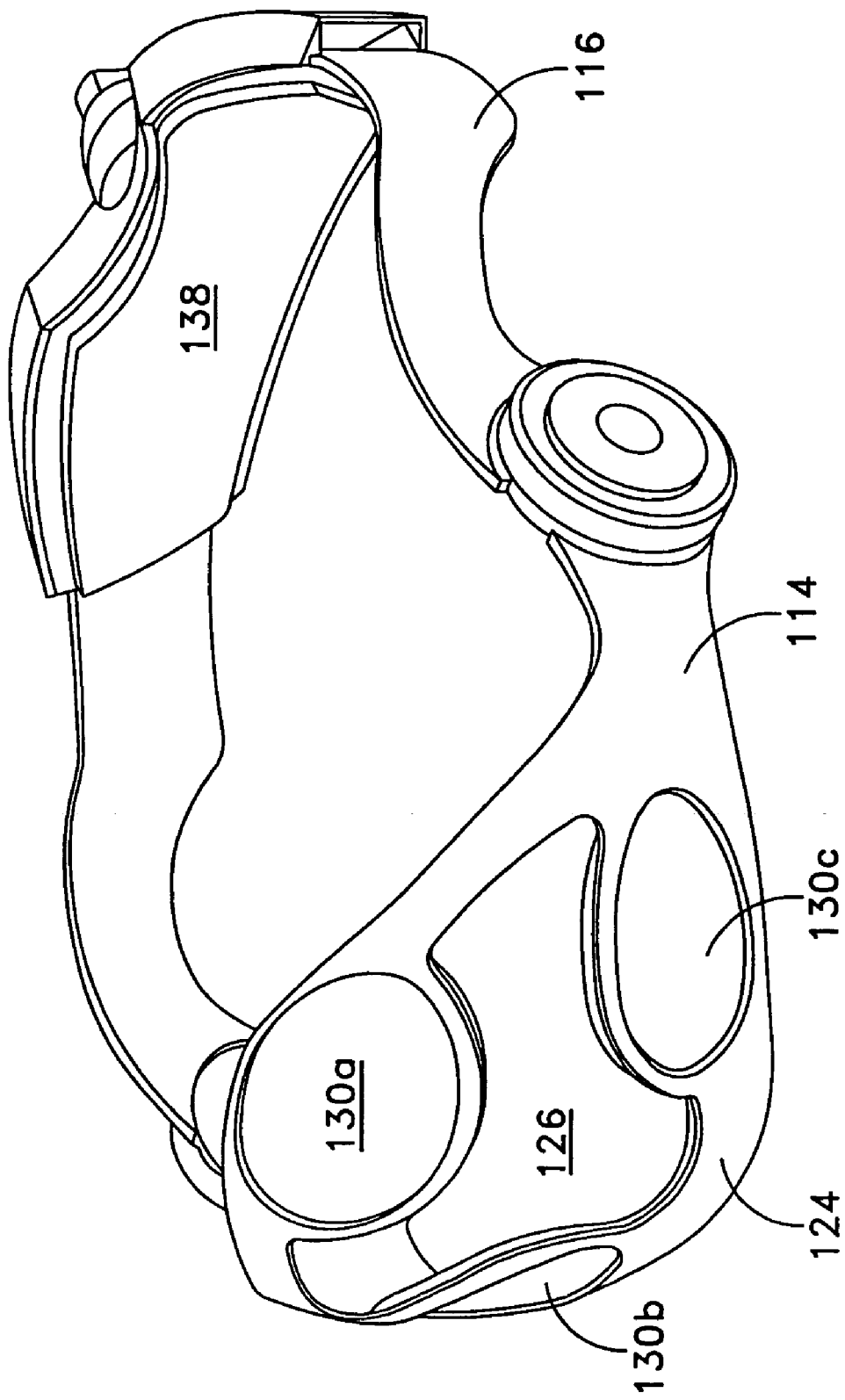
FIG. 16 is a front perspective view of the face shield support of FIG. 15.
Figure 18:
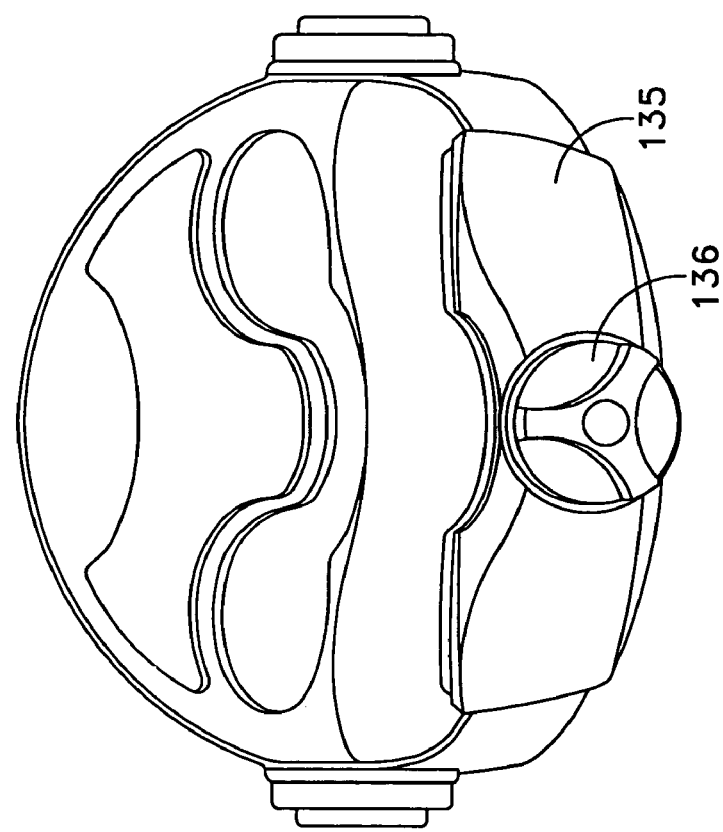
FIG. 18 is a rear elevational of the face shield support of FIG. 15.
Figure 17:
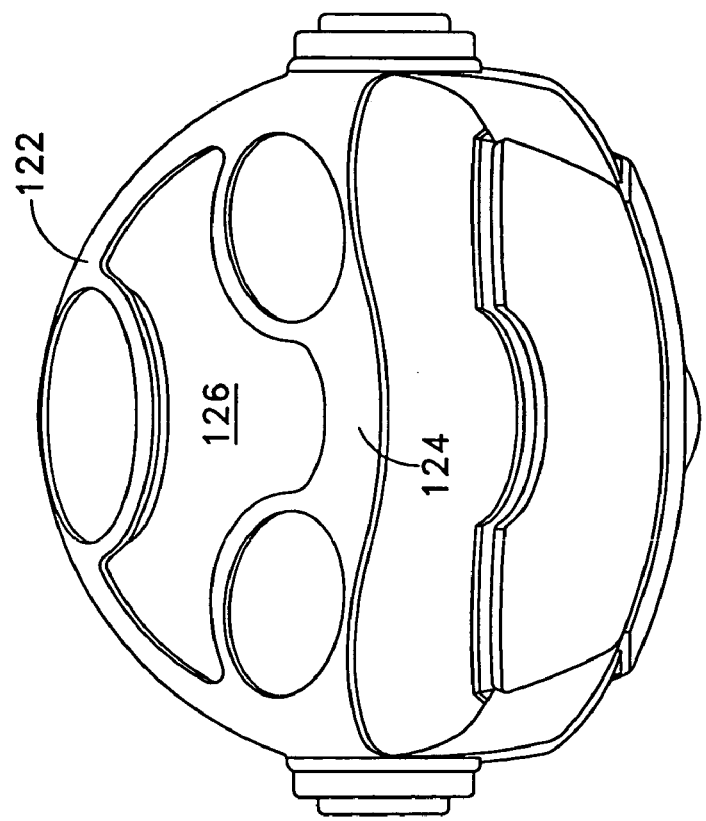
FIG. 17 is a front elevational of the face shield support of FIG. 15.
Figure 19:
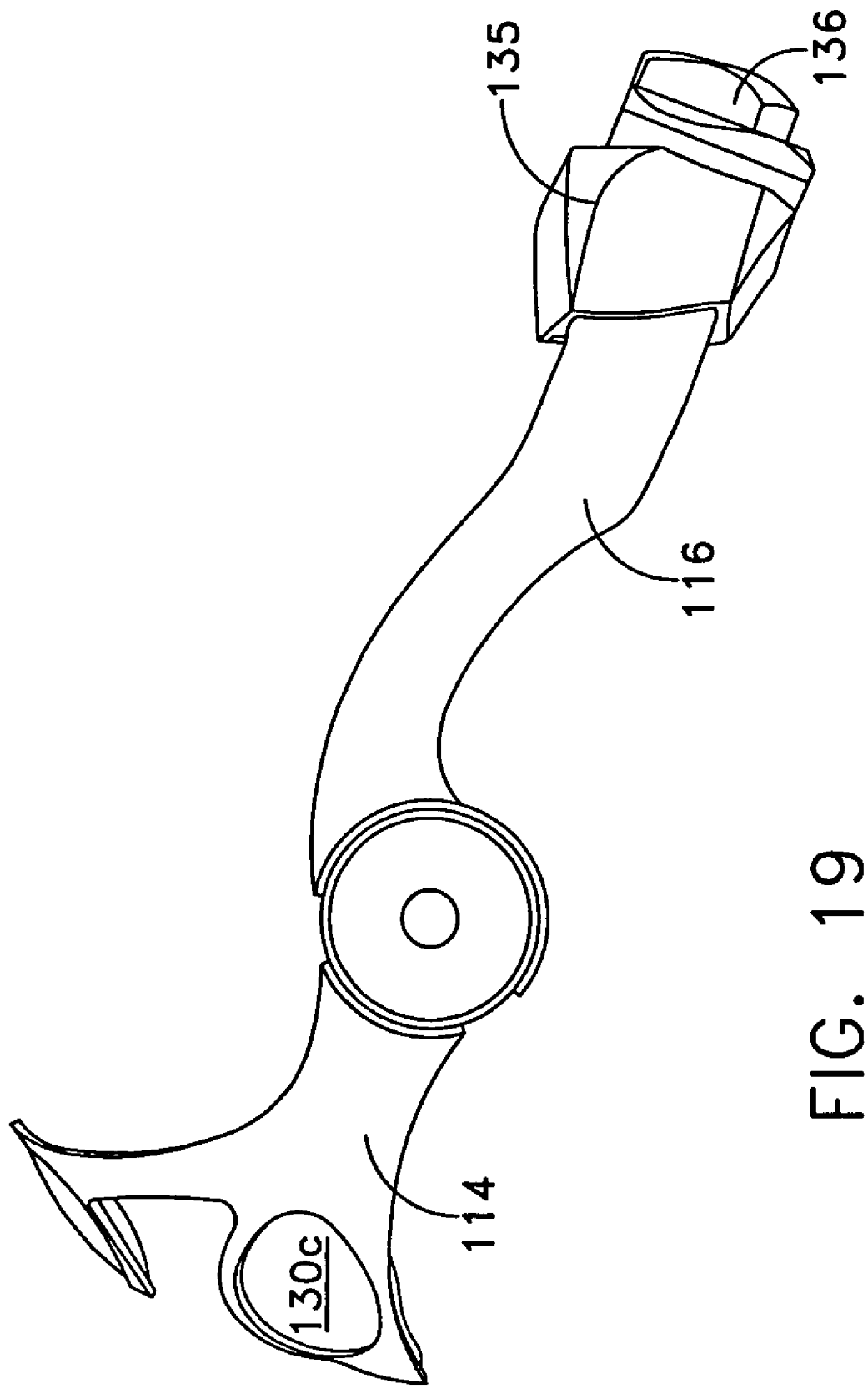
FIG. 19 is a side elevational of the face shield support of FIG. 15.
Figure 21:
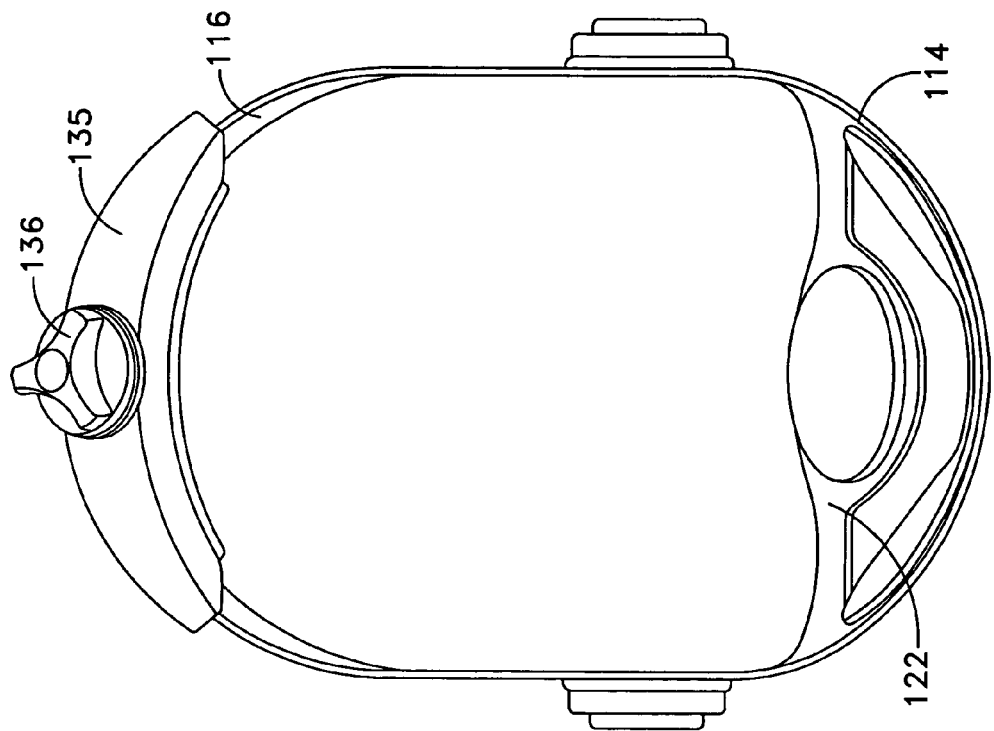
FIG. 21 is a bottom plan view of the face shield support of FIG. 15.
Figure 20:
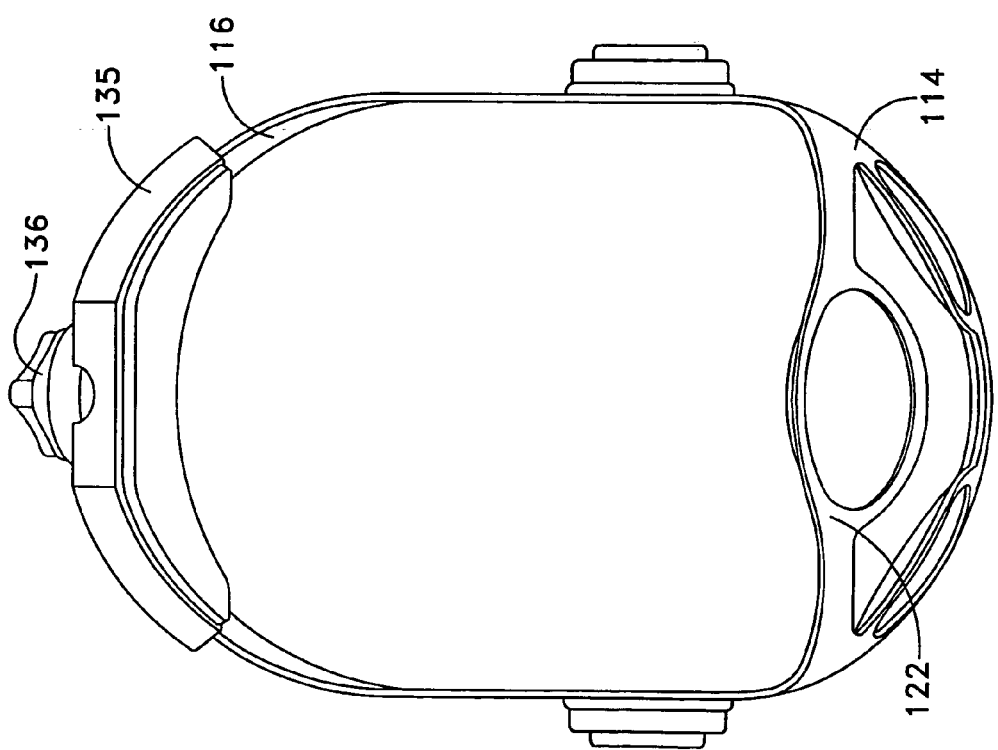
FIG. 20 is a top plan view of the face shield support of FIG. 15.
Figure 22:
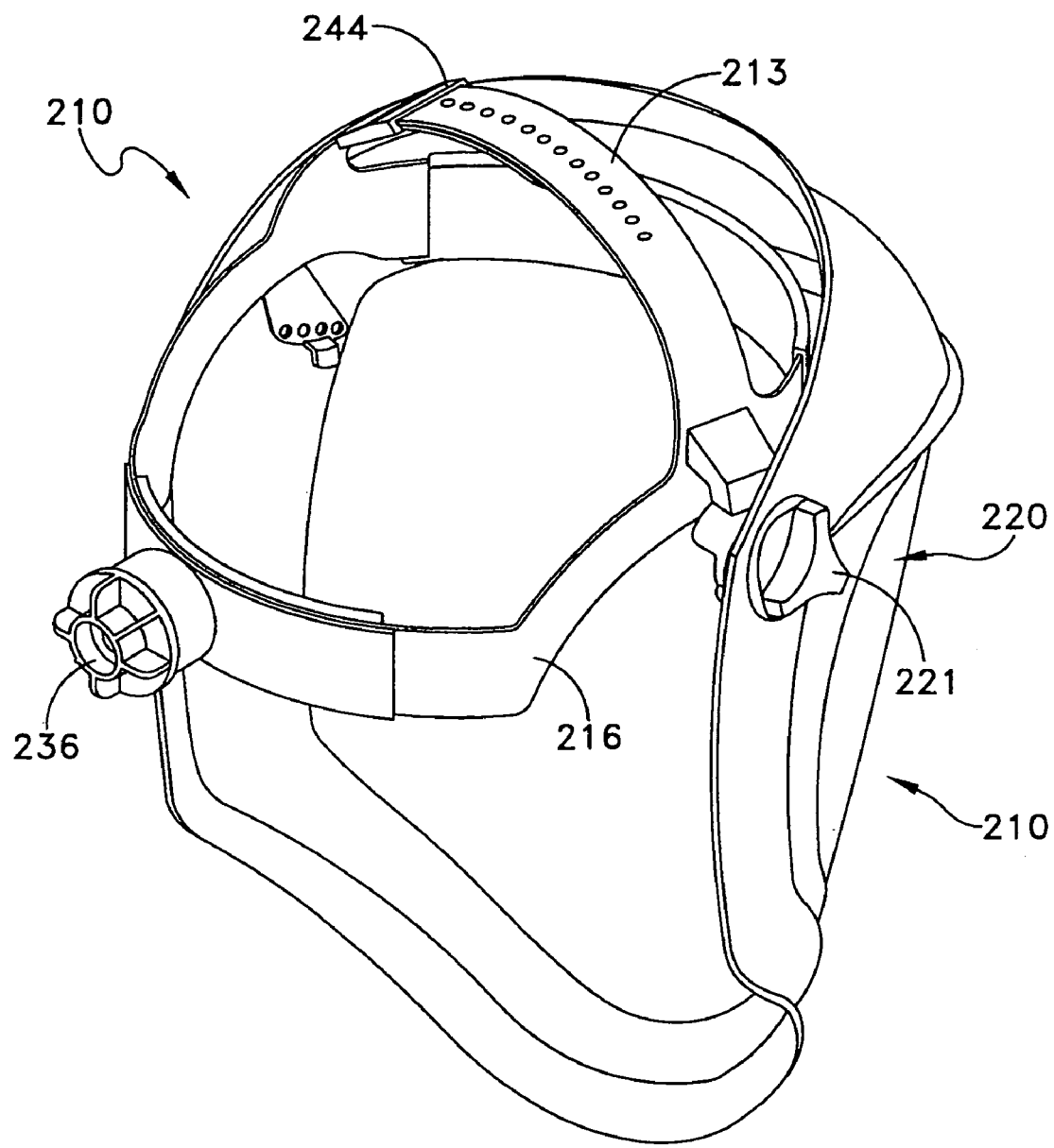
FIG. 22 is a rear perspective view of a third embodiment of a face shield support supporting a face shield.
Figure 23:
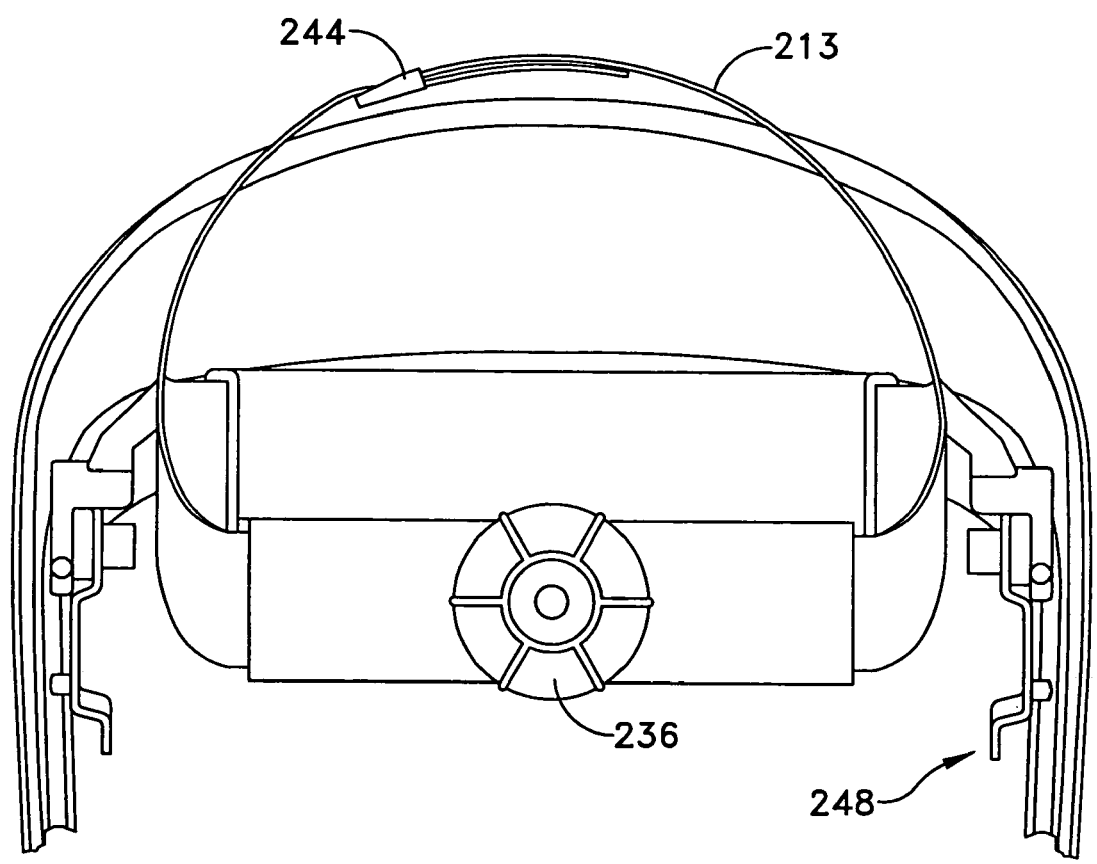
FIG. 23 is a rear, enlarged elevational view of the face shield support of FIG. 22.

Referring now to FIGS. 13 and 14, the rear strap 16 preferably includes a first end 32a and a second end 32b which can be adjusted relative to each other in order to change the overall circumference of the support frame. Such adjustable straps are known in the art and may take any of a variety of known forms. In the present embodiment, the first and second ends of the rear strap are preferably received within housing 35 and are adjusted by rotating knob 36 in either a clockwise or counter clockwise direction to move the first and second ends toward or away from each other, as desired, in order to adjust the circumference of the support frame. A pad 38 (FIG. 2) may be provided on the inside surface of the housing 35 again to provide additional cushioning between the housing and the wearer and may aid with absorption of sweat. Multiple pads 38 may also be provided as shown in FIG. 9. The housing 35 may also support a rear bridge portion 27 which has an inverted "V" configuration in the present embodiment. See FIG. 1. Rear bridge portion 27 may be attached to the frontal bridge portion 23 by a top strap 43 in order to secure the support over the head of the user.

Figure 10:
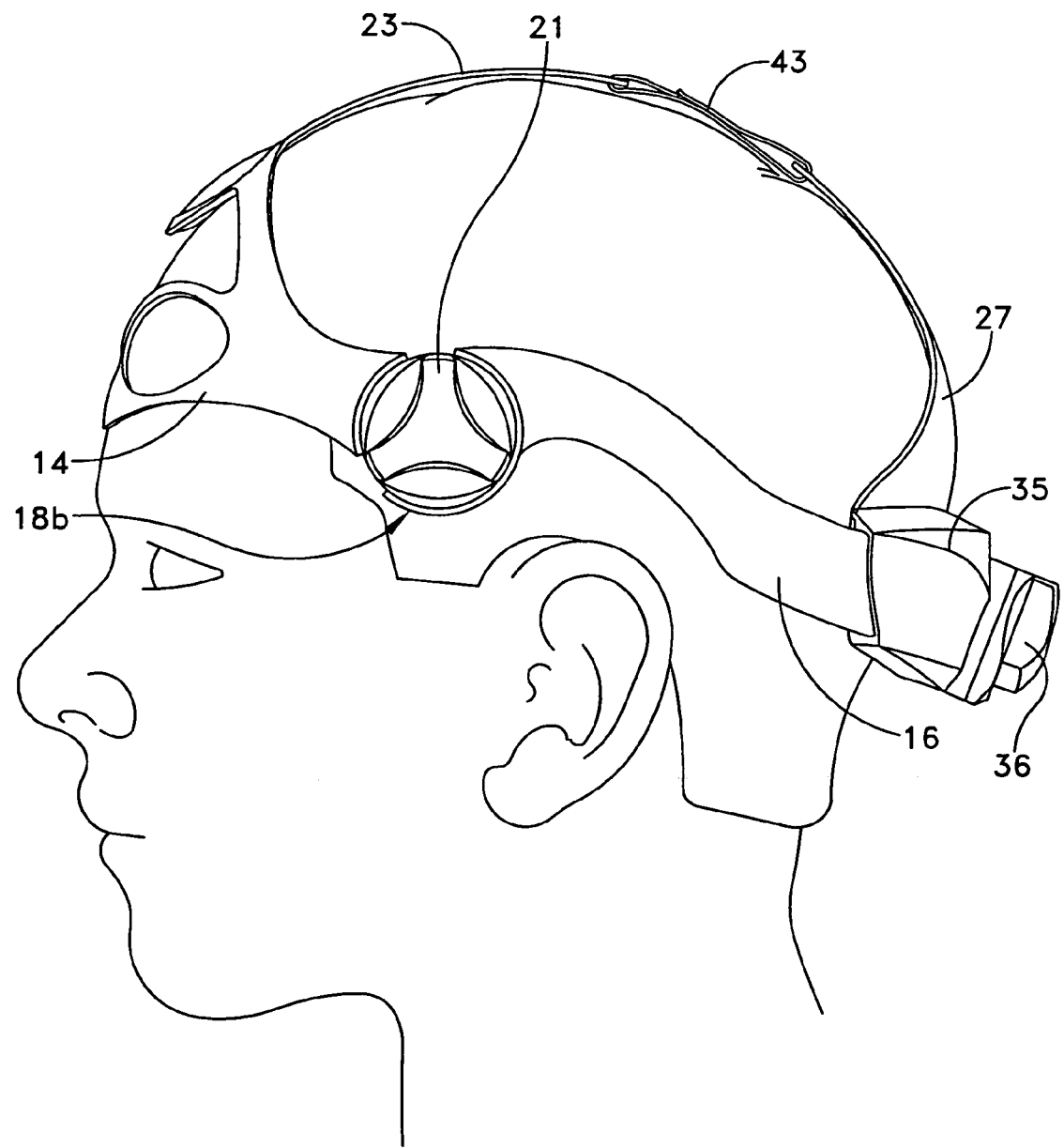
FIG. 10 is a side, perspective view of the face shield support of FIG. 1 on a user.
Figure 11:
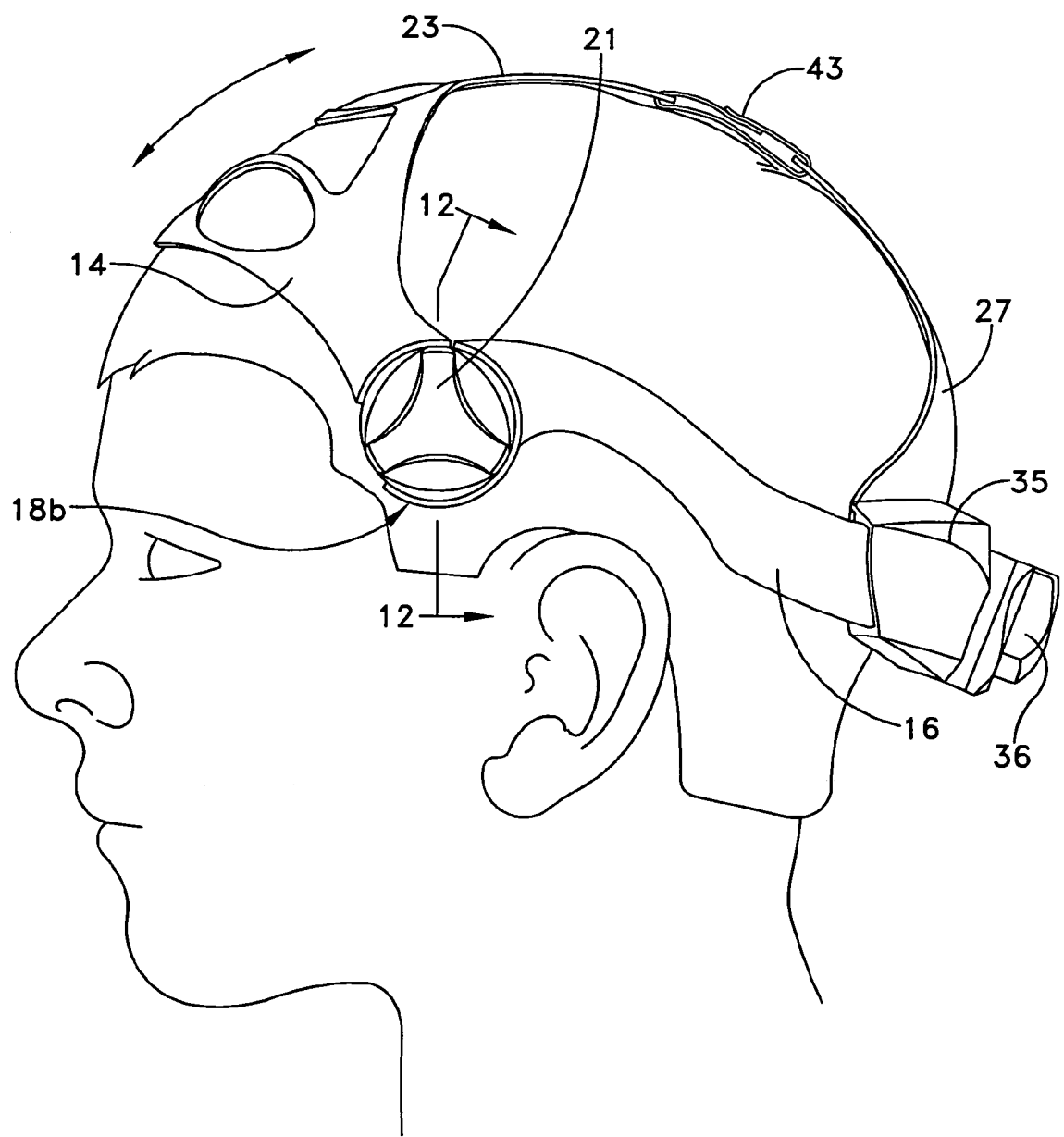
FIG. 11 is a side, perspective view of the face shield support of FIG. 1 on a user showing rotation of the front strap.
Figure 12:
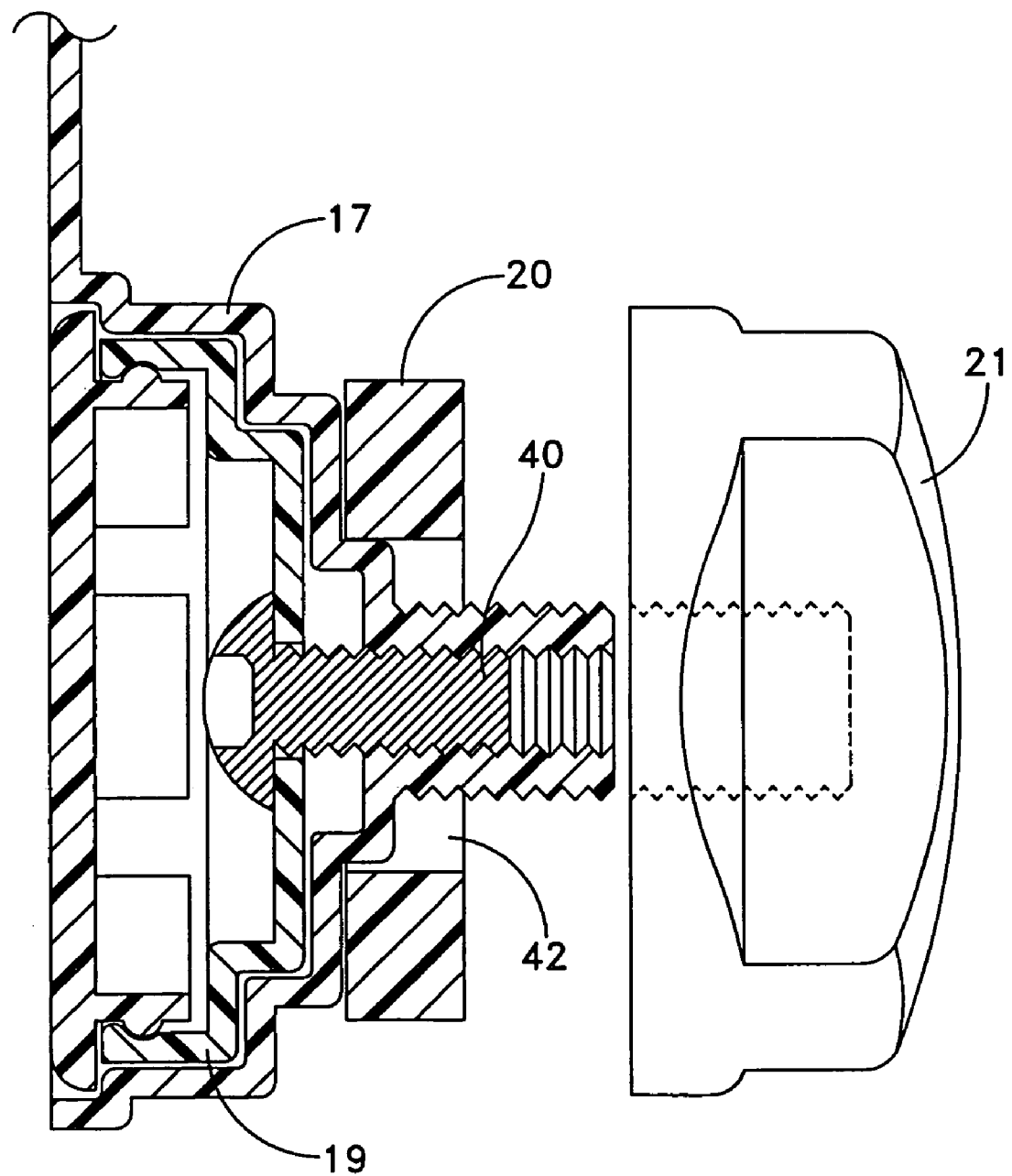
FIG. 12 is a cross sectional view taken along lines 12—12 of FIG. 11.

Use of face shield support will now be described with reference to the Figures. In use, the face shield support is placed over the head of the user as shown in FIGS. 10 and 11. Once on the head of the user, the circumference may be adjusted by rotating the rear knob to either move the first and second ends toward each other (for a smaller circumference) or by moving them away from each other (for a larger circumference). The support may be further adjusted over the top of the user's head by tightening or loosening the top strap in order to move the frontal bridge portion and rear bridge portion either closer or further apart. Once adjusted around and over the head of the user, the frontal strap may be raised or lowered, as desired, to raise or lower the face shield. In order to either raise or lower the frontal strap the side knobs must be loosened and the frontal strap pivoted. Once moved upward or downward the frontal strap can be held in that position by tightening the side knobs. As illustrated in FIG. 11, when moved upward the expanded frontal area sits on the upper portion of the head, and in the power position, as shown in FIG. 10, sits on the forehead of the user. In either position, the frontal area distributes pressure of the face shield.

Referring now to FIGS. 15–21 a second, alternate embodiment of the face shield support is shown. In this embodiment, all parts which are the same, or similar to, corresponding parts in the first embodiment are noted with the same two last numbers, but preceded by the numeral "1". As illustrated, the face shield support 110 is identical to support 10 described above, with the exception of the bridge formed by the frontal bridge portion and rear bridge portion which is eliminated in the present embodiment. Otherwise, the support is the same as that described above with reference to FIGS. 12–21 and is likewise adjustable to change the circumference of the support and the frontal bridge portion is pivotal to move between an upward and a downward position.

A third, alternate embodiment is illustrated in FIGS. 22–32. In this embodiment, all parts which are the same, or similar to, corresponding parts in the first embodiment are noted with the same two last numbers, but preceded by the numeral "2". The face shield support 210 of the present embodiment preferably includes a circumferentially, adjustable strap 216 that extends around the circumference of the user's head during operation over the forehead and occipital lobe, and a second, adjustable top strap 213 that extends over a top portion of the user's head during use. Such adjustable circumferential and top straps are known in the art and may be adjusted in any of a variety of known ways. For example, a knob 236 may be provided to adjust the size of the circumferential strap 216, while a buckle style adjustment 244 may be utilized to adjust the top strap 213, as shown in the present embodiment. The adjustability allows for a more comfortable, custom fit of the support structure on the head of the user.

Figure 24:
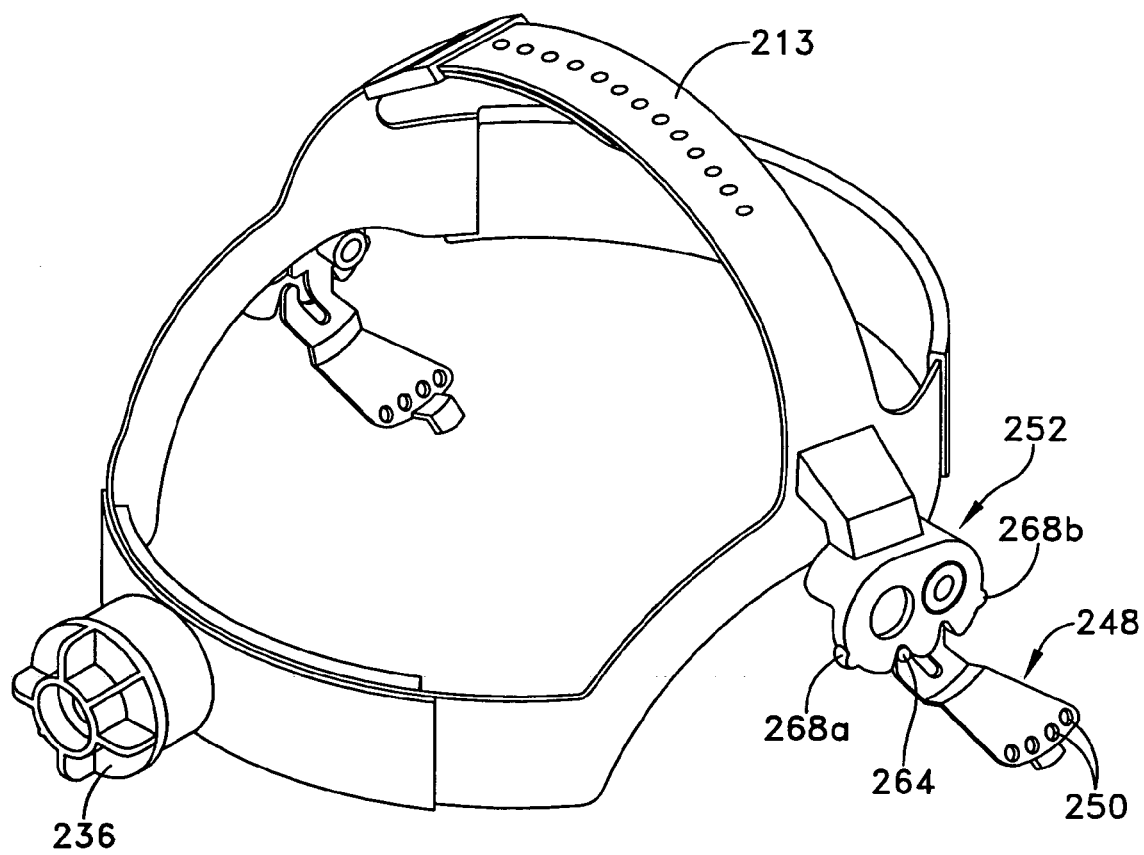
FIG. 24 is a rear perspective view of the face shield support of FIG. 22.
Figure 25:
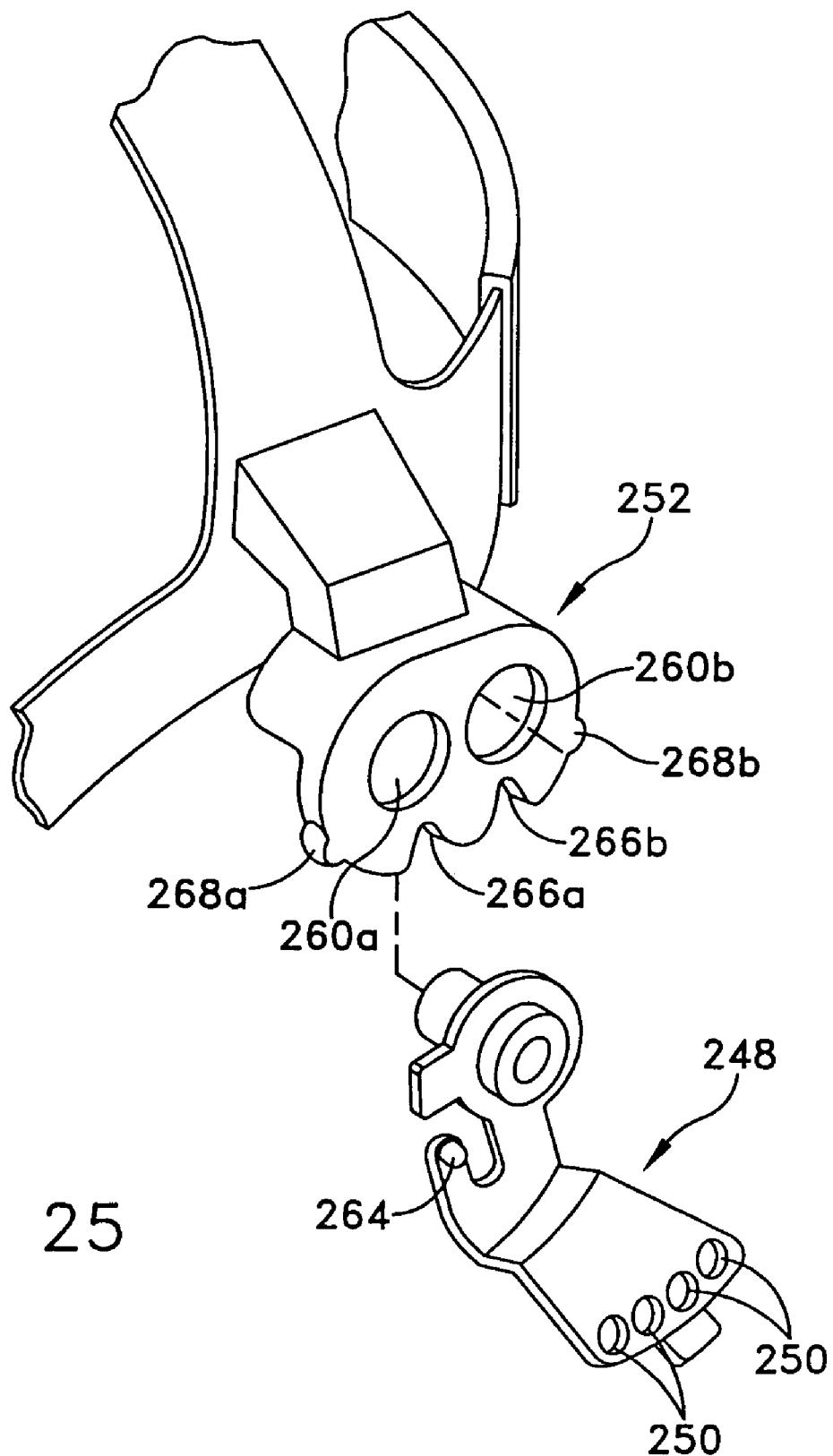
FIG. 25 is an enlarged, exploded view of a mounting device of the support structure of FIG. 22.

Mounting members 252 are preferably provided to support the face shield 220 on the support member 210. In the present embodiment, as shown in FIGS. 24 and 25, a fixed mounting element 248 having a plurality of mounting holes 250 is secured to an inner surface of either side of the face shield. A corresponding, adjustable mounting element 252 is supported on either side of the circumferential strap 216, preferably above and adjacent the user's ears. In the present embodiment, the corresponding adjustable mounting elements are supported below the juncture of the top strap 213 and the circumferential adjustable strap 216. A pair of mounting holes 260a, 260b may be provided on the adjustable mounting element 252 so that the face shield may be selectively positioned relative to the user's face. A pair of knobs 221, each having a pin (not shown) are preferably utilized to support the adjustable mounting elements 252 to the face shield. If the pin is received through a distal mounting hole 260b a gap, "$G_D$" (FIG. 28), is formed between the user's face and an inner surface of a lens of the face shield. However, if the pin is received through a proximal mounting hole 260a a gap, "$G_P$" (FIG. 32), is formed between the user's face and an inner surface of the lens of the face shield. As will be appreciated the distance between the user's face and the inner surface of the lens is greater for gap $G_D$ than for gap $G_P$. This allows the user to choose a specific spacing, as desired, during a particular operation. For example, if the user is wearing goggles with the face shield (as is common for many applications) then the user will probably choose to use the distal mounting hole 260b in order to create a greater gap and, hence, room for the goggles.

Figure 28:
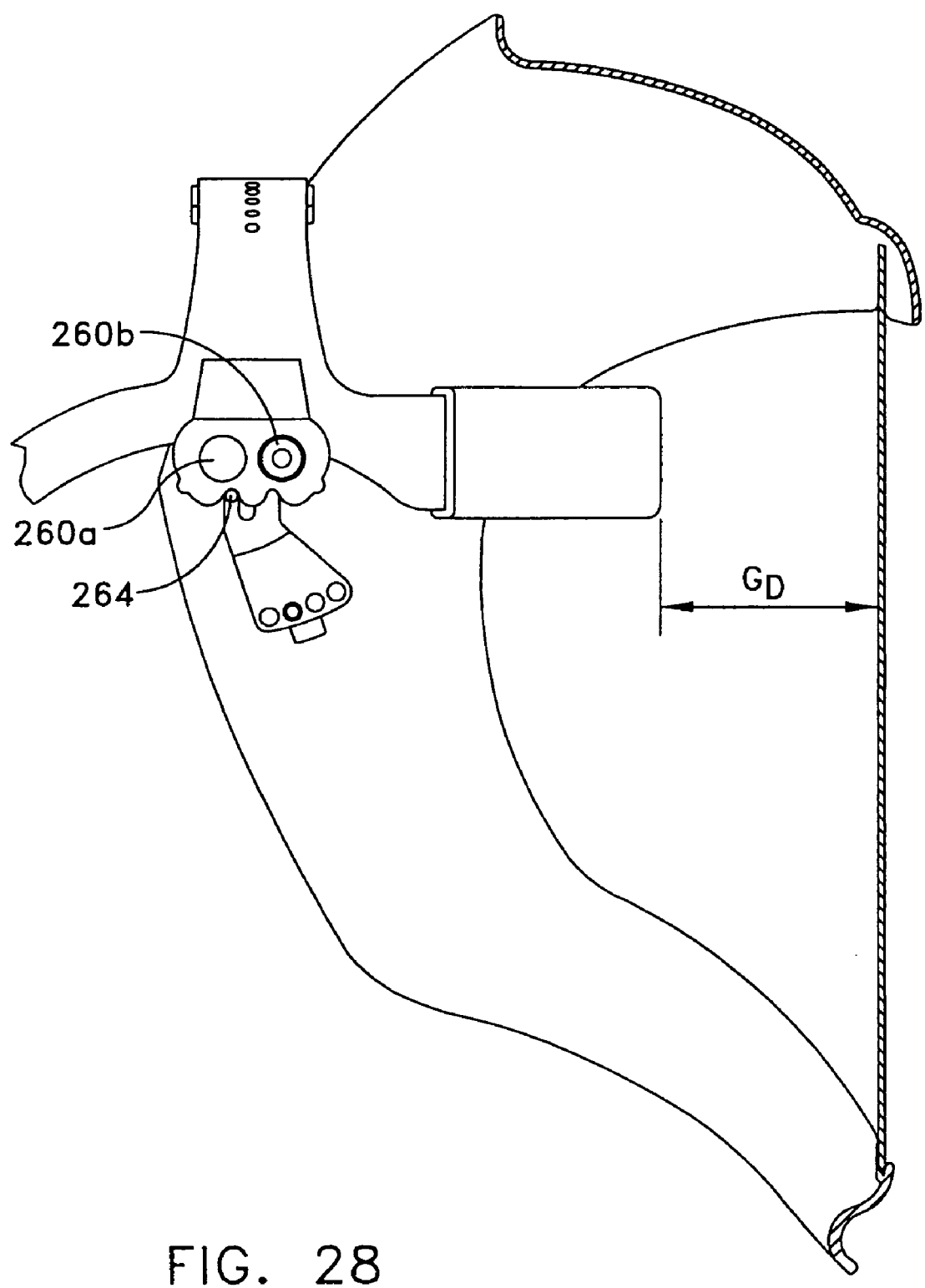
FIG. 28 is a side view illustrating the face shield support of FIG. 22 with the face shield in a down position and having a first distance between the user and the face shield lens.
Figure 29:
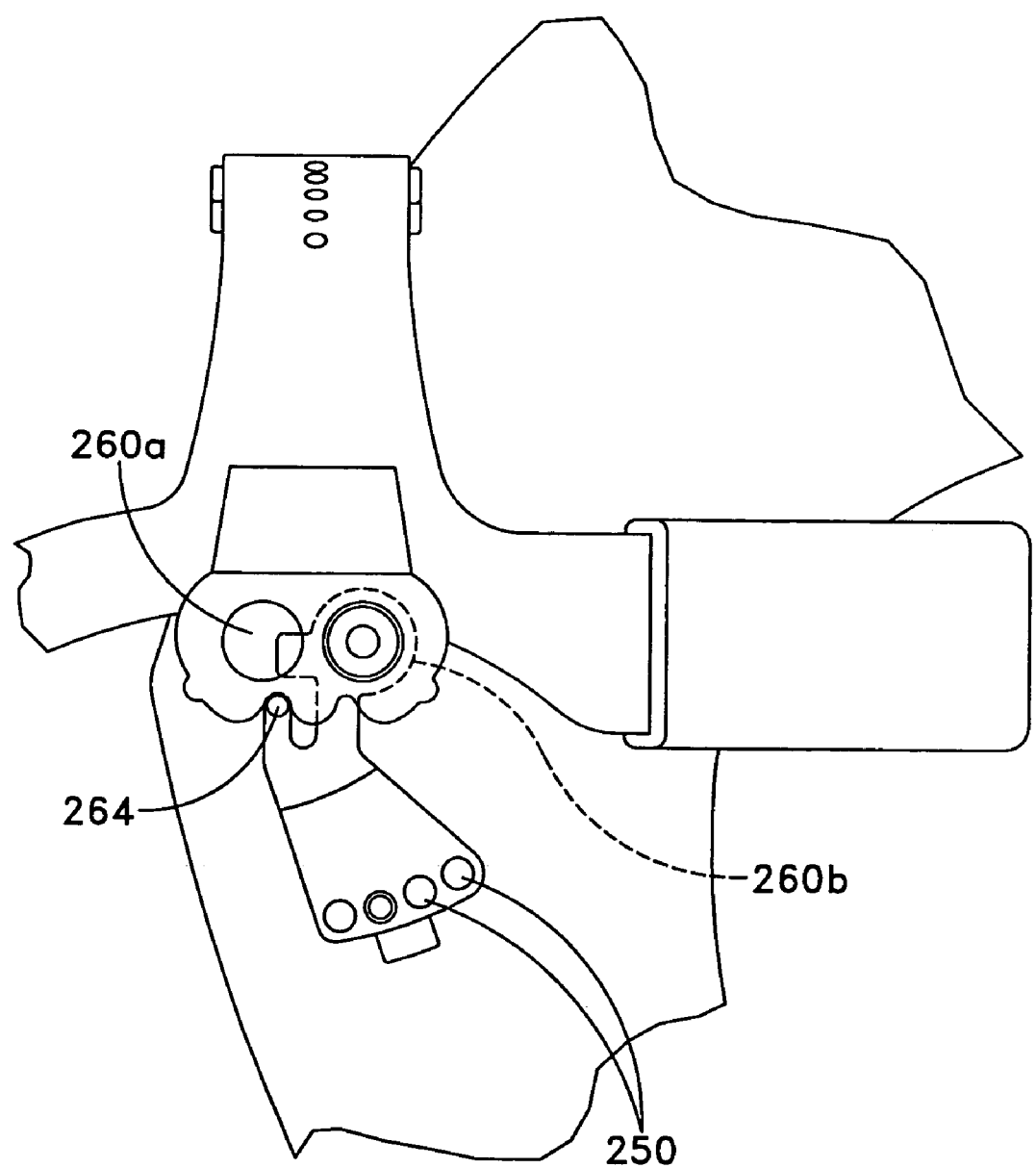
FIG. 29 is an enlarged view of the face shield support of FIG. 28.
Figure 30:
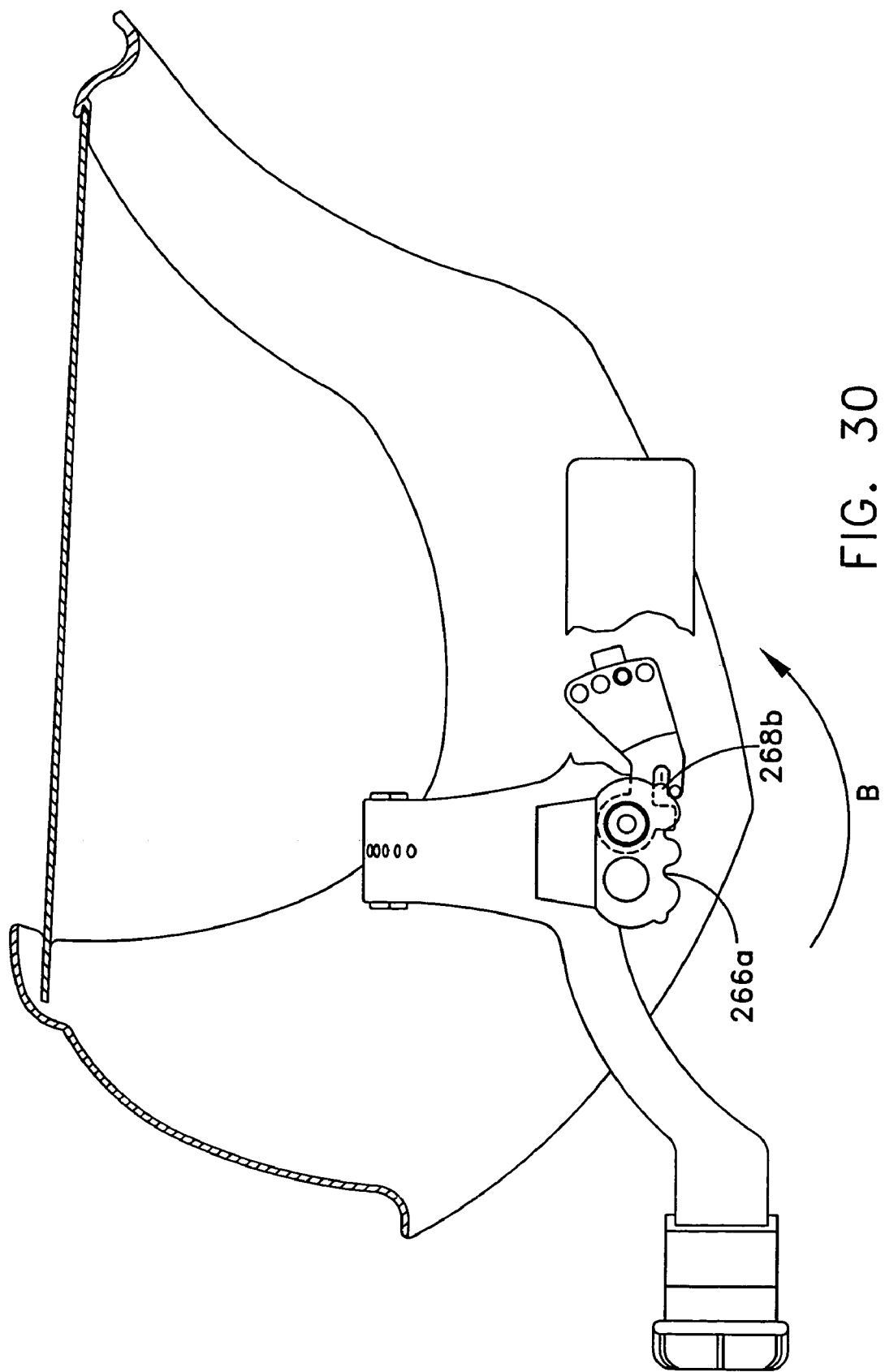
FIG. 30 is a side view illustrating the face shield support of FIG. 22 with the face shield in an up position.
Figure 31:
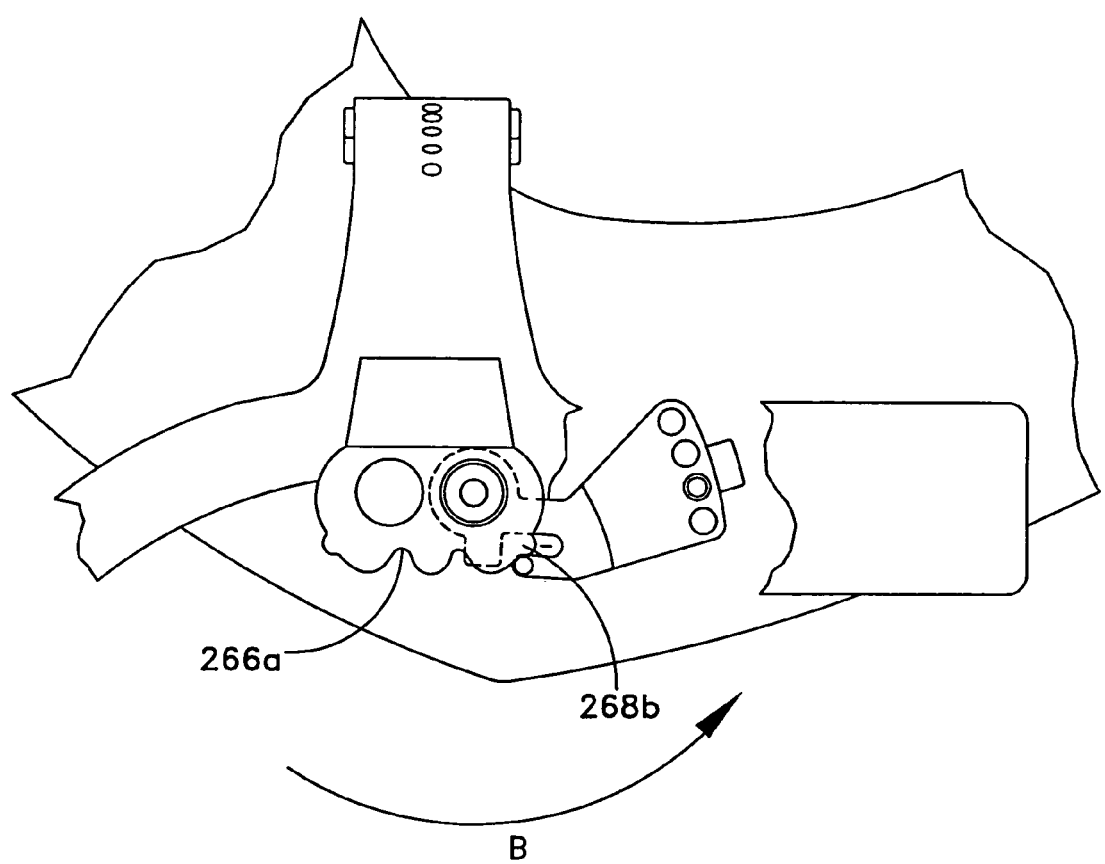
FIG. 31 is an enlarged view of the face shield support of FIG. 30.
Figure 32:
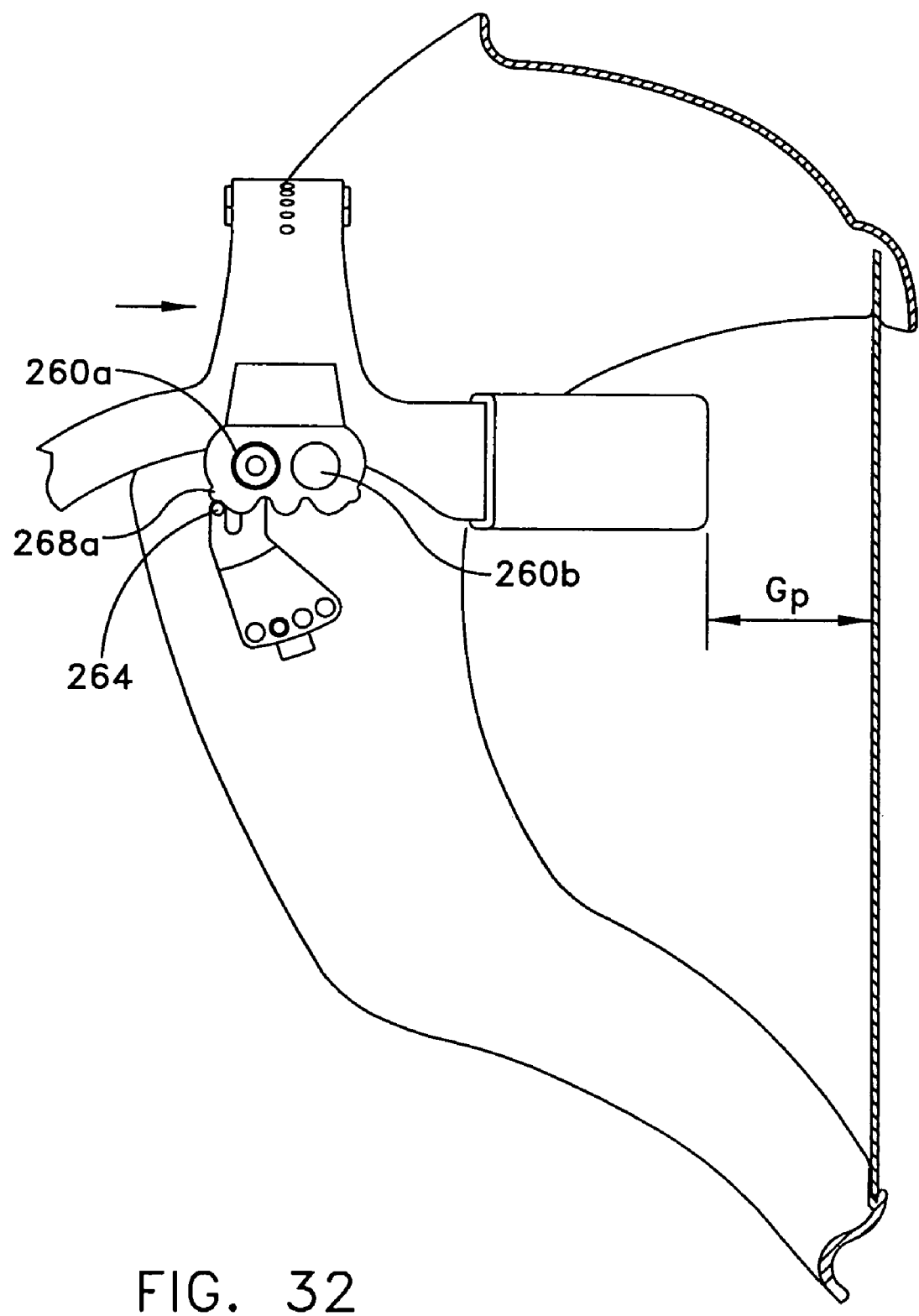
FIG. 32 is a side view illustrating the face shield support of FIG. 22 with the face shield in a down position and having a first distance between the user and the face shield lens.
Figure 33:
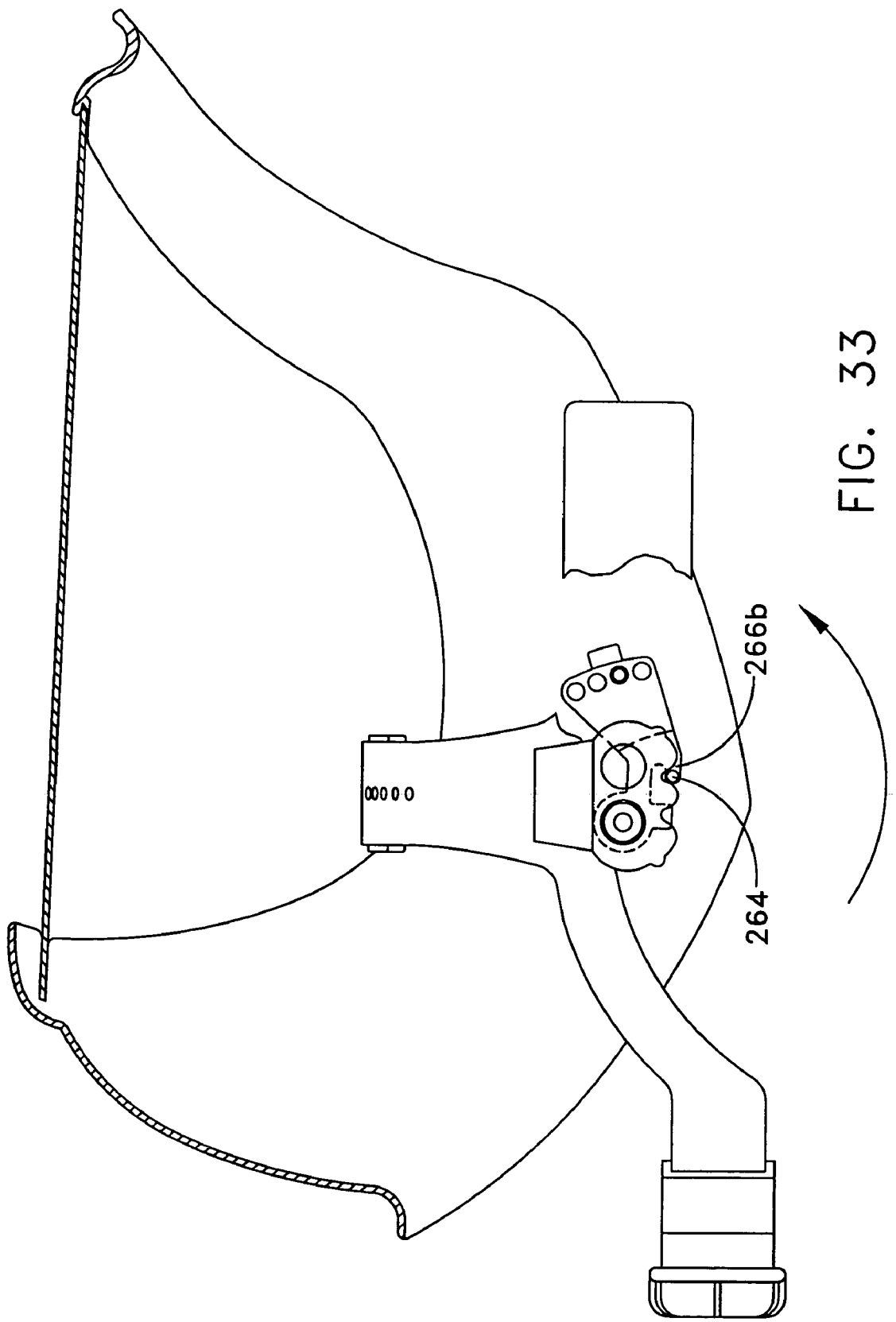
FIG. 33 is a side view illustrating the face shield support of FIG. 32 with the face shield in an up position.

In addition to being able to create an adjustable gap, the mounting members 252 also preferably include a pin 264 that is selectively engageable with at least two notches 266a, 266b disposed in the mounting member 252 in order to restrain the face shield in either the upper or lower positions. In the present embodiment, the pin is supported on the fixed mounting element and the at least two notches are formed in the adjustable mounting element, although the reverse configuration may also be utilized. A pair of stops 268a, 268b may also be provided in order to limit the movement of the face shield during use. For example, when the face shield is supported on the face shield support by the distal mounting hole 260b it is in the lowered position, i.e., is covering the face of the user. In such a case, the pin 264 is received within the first notch 266a as shown in FIG. 28. In order to move the face shield into the upper position, the user would lift the face shield in the direction of arrow "B" (FIG. 30) thus moving the pin out of the first notch 266a and into engagement with stop 268b. If, however, the face shield is supported on the support structure by the proximal mounting hole 260a and is in the lowered position the pin 264 would be in engagement with stop 268a (FIG. 32). As the face shield is lifted into the upper position, the pin would move into the second notch 266b as shown in FIG. 33. In this manner, the face shield is supported in either the upper or lower position until moved by the user.

In use, the support of the third embodiment is placed on the head of the user. Once on the head of the user, the circumference may be adjusted by rotating the rear knob to either move the first and second ends toward each other (for a smaller circumference) or by moving them away from each other (for a larger circumference). The support may be further adjusted over the top of the user's head by tightening or loosening the top straps. The user can then chose to engage either the distal or proximal mounting holes in order to position the lens relative to their face, as desired. For example, if the user is wearing goggles the lens may be positioned further from the user's face in order to make room for the goggles. The user may then selectively raise and lower the face shield frame, as desired, with at least two notches and stops holding the frame in position and limiting movement of the shield.

Figure 34:
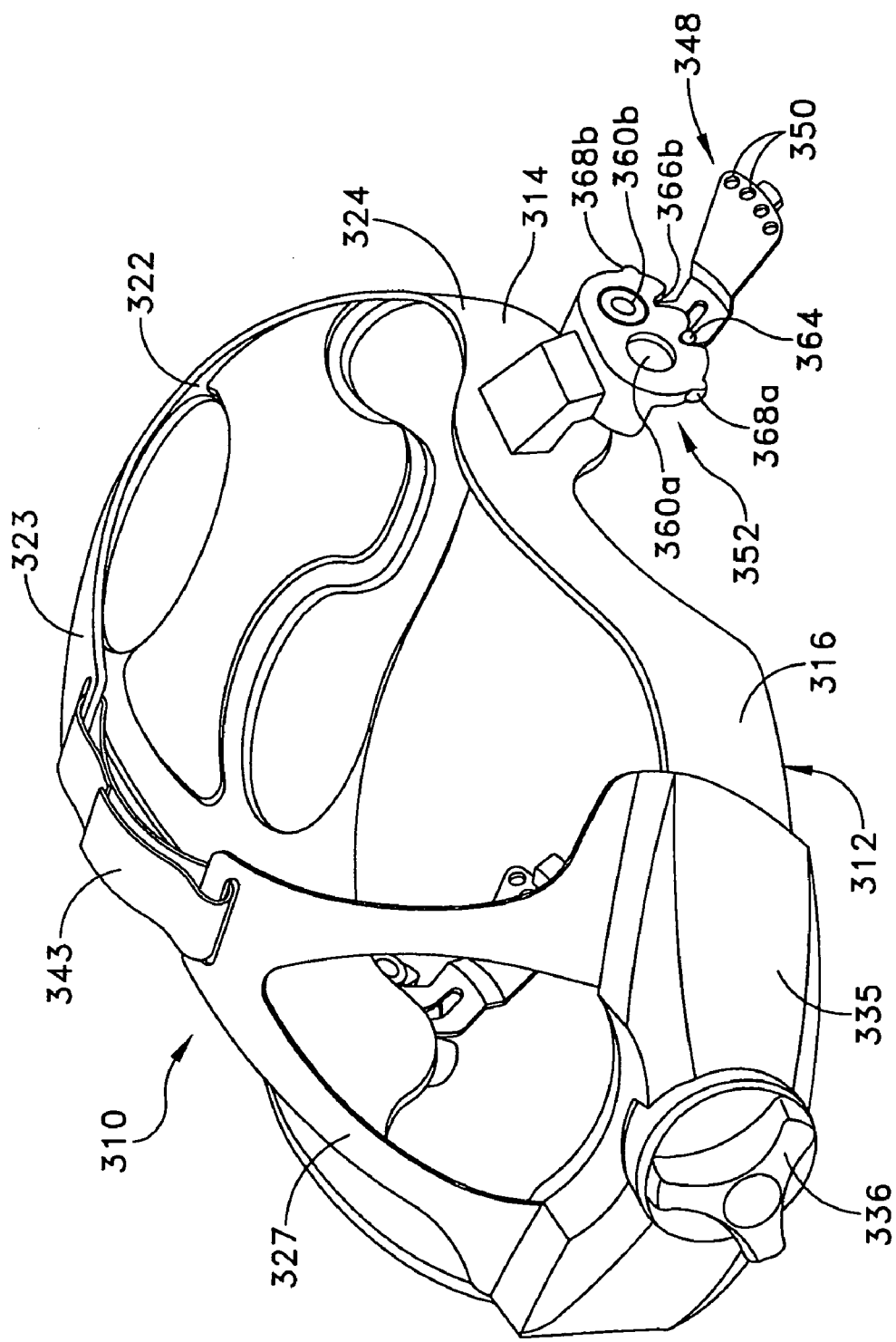
FIG. 34 is a rear perspective view of a forth embodiment of a face shield support for supporting a face shield.

Referring now to FIG. 34, a fourth embodiment of the face shield support is illustrated. In this embodiment, all parts which are the same, or similar to, corresponding parts in the previous embodiments are noted with the same two last numbers, but preceded by the numeral "3". The face shield support 310 of the fourth embodiment is a combination of features from the first and third embodiment. Specifically, the face shield frame 312 is the same as described with respect to the first embodiment, while the mounting members 352 are the same as those described above with respect to the third embodiment. As illustrated, there is an expanded frontal area which may include an upper portion 322 and a lower portion 324 which together form a generally triangular configuration as described above with respect to the first embodiment. The upper portion 322 may also support a frontal bridge portion 323 for attachment with a rear bridge portion 327 by a strap 343. The frontal and rear bridge portions help secure the support over the head of the wearer, as described in greater detail above. The rear strap 316 may also preferably include a first end and a second end which can be adjusted relative to each other in order to change the overall circumference of the support frame. The first and second ends of the rear strap may be received within housing 335 and are adjusted by rotating knob 336 in either a clockwise or counter clockwise direction to move the first and second ends toward or away from each other, as desired, as also described above.

Mounting members including a fixed mounting element 348 having a plurality of mounting holes 350 secured to an inner surface of either side of the face shield and a corresponding adjustable mounting element 352 supported on the support frame 312 are preferably provided as described above. A pair of mounting holes 360a, 360b may be formed on the adjustable mounting element 352 so that the face shield may be selectively positioned relative to the user's face as also described above with respect to the third embodiment. A pair of knobs (not shown), each having a pain (not shown) are preferably utilized to support the adjustable mounting element 352 to the face shield.

It will be understood that various modifications may be made to the embodiments disclosed herein. For example, not all components disclosed need be utilized, such as the pads and bridge member, etc. In addition, the shapes and sizes of the support disclosed herein may also be changed, as would be known to those of skill in the art. Therefore, the above description should not be construed as limiting, but merely as exemplifications of preferred embodiments. Those skilled in the art will envision other modifications within the scope, spirit and intent of the invention.

The invention claimed is:

1. A support for a face shield, comprising:
   a frame adapted to fit over a head of a user and including;
   a.) at least a front strap and a rear strap constructed and arranged to fit around a circumference of the head of the user, the front strap including an expanded frontal area constructed and arranged to distribute pressure over the forehead of the user, the expanded frontal area including an upper portion and a lower portion;
   b.) a pair of mounting members constructed and arranged to support the face shield on the frame and adapted to allow pivotal movement of the face shield between an upper and a lower position;
   and at least one additional bridge strap that interconnects between the front and rear straps and that is for placement over the top of the head of the user.

2. The support of claim 1, wherein the expanded frontal area includes an opening disposed between the upper portion and the lower portion of the front strap.

3. The support of claim 2, wherein the expanded frontal area has a generally triangular shape.

4. The support of claim 1, wherein said at least one additional bridge strap comprises a frontal bridge portion and a rear bridge portion, the frontal and rear bridge portions extending over a top of the head of the user.

5. The support of claim 4, wherein the frontal and rear bridge portions are adjustable relative to each other in order to selectively adjust the support over the top of the head of the user.

6. A support for a face shield, comprising:
   a frame adapted to fit over a head of a user and including;
   a.) at least a front strap and a rear strap constructed and arranged to fit around a circumference of the head of the user, the front strap including an expanded frontal area constructed and arranged to distribute pressure over the forehead of the user, the expanded frontal area including an upper portion and a lower portion; and
   b.) a pair of mounting members constructed and arranged to support the face shield on the frame and adapted to allow pivotal movement of the face shield between an upper and a lower position;
   and a frontal bridge portion and a rear bridge portion, the frontal and rear bridge portions extending over a top of the head of the user.

7. The support of claim 6, wherein the frontal and rear bridge portions are adjustable relative to each other in order to selectively adjust the support over the top of the head of the user.

8. A support for a face shield, comprising:
   a frame that includes a front strap and a rear strap that are together constructed and arranged to fit around a circumference of the head of the user with the front strap including an expanded frontal area constructed and arranged to distribute pressure over the forehead of the user;
   the expanded frontal area of the front strap including an upper portion and a lower portion;
   said upper and lower portions defining therebetween an opening at the location of the forehead of the user to allow air to circulate;
   a pair of mounting members constructed and arranged to support the face shield from the frame and adapted to allow pivotal connection between the front and rear straps;
   each mounting member including a pair of mating relatively rotatable collars that connect respectively with the front and rear straps and an adjustment knob connecting the collars;
   said adjusting knob in its loose position permitting limited relative movement between the collars to allow relative positioning between the straps supported thereby and, in its tightened position, holding the relative position between the collars and correspondingly the straps.

9. The support of claim 8 further including at least one additional bridge strap that interconnects between the front and rear straps and that is for placement over the top of the head of the user.

10. The support of claim 8 including a frontal bridge portion and a rear bridge portion, the frontal and rear bridge portions extending over a top of the head of the user.

11. The support of claim 8 wherein said pair of collars include an inner collar and an outer collar and said inner collar connects with said rear strap and said outer collar connects with said front strap.

* * * * *